United States Patent
Lindsay et al.

(10) Patent No.: US 10,139,417 B2
(45) Date of Patent: Nov. 27, 2018

(54) SYSTEMS, APPARATUSES AND METHODS FOR READING AN AMINO ACID SEQUENCE

(71) Applicant: ARIZONA BOARD OF REGENTS acting for and on behalf of ARIZONA STATE UNIVERSITY, Scottsdale, AZ (US)

(72) Inventors: Stuart Lindsay, Phoenix, AZ (US); Peiming Zhang, Gilbert, AZ (US); Yanan Zhao, Tempe, AZ (US)

(73) Assignee: ARIZONA BOARD OF REGENTS ON BEHALF OF ARIZONA STATE UNIVERSITY, Scottsdale, AR (US)

( * ) Notice: Subject to any disclaimer, the term of this patent is extended or adjusted under 35 U.S.C. 154(b) by 168 days.

(21) Appl. No.: 14/376,154

(22) PCT Filed: Jan. 31, 2013

(86) PCT No.: PCT/US2013/024130
§ 371 (c)(1),
(2) Date: Aug. 1, 2014

(87) PCT Pub. No.: WO2013/116509
PCT Pub. Date: Aug. 8, 2013

(65) Prior Publication Data
US 2015/0010935 A1 Jan. 8, 2015

Related U.S. Application Data

(60) Provisional application No. 61/593,552, filed on Feb. 1, 2012, provisional application No. 61/647,847, filed on May 16, 2012.

(51) Int. Cl.
*G01N 33/68* (2006.01)
*G01N 33/487* (2006.01)

(52) U.S. Cl.
CPC ... *G01N 33/6821* (2013.01); *G01N 33/48721* (2013.01)

(58) Field of Classification Search
None
See application file for complete search history.

(56) References Cited

U.S. PATENT DOCUMENTS 8,628,649 B2   1/2014   Lindsay et al.
8,961,757 B2   2/2015   Nuckolls et al.
(Continued)

FOREIGN PATENT DOCUMENTS

WO   WO2008124706 A2   10/2008
WO   WO2009117517 A2   9/2009
(Continued)

OTHER PUBLICATIONS

Wikipedia, http://web.archive.org/web/20100304090000/http://en.wikipedia.org/wiki/Proteasome, archived Mar. 4, 2010, accessed Nov. 17, 2016.*

(Continued)

*Primary Examiner* — Erin M. Bowers
(74) *Attorney, Agent, or Firm* — Schwabe, Williamson & Wyatt, P.C.

(57) ABSTRACT

Embodiments of the present disclosure relate to amino acid, modified amino acid, peptide and protein identification and sequencing, by means of, for example, electronic detection of individual amino acids or small peptides.

9 Claims, 26 Drawing Sheets

(56) References Cited

U.S. PATENT DOCUMENTS

| | | | |
|---|---|---|---|
| 8,968,540 B2 | 3/2015 | Reinhart et al. | |
| 9,140,682 B2 | 9/2015 | Lindsay et al. | |
| 9,274,430 B2 | 3/2016 | Gyarfas et al. | |
| 9,395,352 B2 | 7/2016 | Lindsay et al. | |
| 9,593,372 B2 | 3/2017 | Lindsay et al. | |
| 9,766,248 B2 | 9/2017 | Lindsay et al. | |
| 9,810,681 B2 | 11/2017 | Lindsay et al. | |
| 2003/0089605 A1* | 5/2003 | Timperman | B01L 3/5027 204/450 |
| 2005/0136408 A1 | 6/2005 | Tom-Moy et al. | |
| 2005/0217990 A1 | 10/2005 | Sibbett et al. | |
| 2006/0073489 A1 | 4/2006 | Li et al. | |
| 2010/0084276 A1 | 4/2010 | Lindsay | |
| 2010/0294659 A1 | 11/2010 | Green | |
| 2010/0310421 A1* | 12/2010 | Oliver | G01N 33/48721 422/82.01 |
| 2013/0302901 A1 | 11/2013 | Lindsay et al. | |
| 2015/0010935 A1 | 1/2015 | Lindsay et al. | |
| 2015/0142327 A1 | 5/2015 | Ashcroft et al. | |
| 2015/0144506 A1 | 5/2015 | Lindsay et al. | |
| 2016/0018384 A1 | 1/2016 | Lindsay et al. | |
| 2016/0097759 A1 | 4/2016 | Lindsay et al. | |
| 2016/0177383 A1 | 6/2016 | Ashcroft et al. | |
| 2016/0194698 A1 | 7/2016 | Lindsay | |
| 2016/0258925 A1 | 9/2016 | Gyarfas et al. | |
| 2016/0280723 A1 | 9/2016 | Zhang et al. | |
| 2017/0003245 A1 | 1/2017 | Lindsay et al. | |
| 2017/0016852 A1 | 1/2017 | Lindsay et al. | |
| 2017/0038369 A1 | 2/2017 | Lindsay et al. | |
| 2017/0067902 A1 | 3/2017 | Zhang et al. | |
| 2017/0137389 A1 | 5/2017 | Zhang et al. | |
| 2017/0204066 A1 | 7/2017 | Lindsay et al. | |
| 2017/0343558 A1 | 11/2017 | Lindsay et al. | |

FOREIGN PATENT DOCUMENTS

| | | | |
|---|---|---|---|
| WO | WO2009117522 A2 | | 9/2009 |
| WO | WO2010042514 A1 | | 4/2010 |
| WO | WO 2011/097171 | * | 8/2011 |
| WO | WO2011097171 A1 | | 8/2011 |

OTHER PUBLICATIONS

Boersma et al., (2012). "Continuous Stochastic Detection of Amino Acid Enantiomers with a Protein Nanopore." Angew. Chem. Int. Ed. 51: 9606-9609.

Cool et al., (2004). "C-Terminal sequencing of peptide hormones using carboxypeptidase Y and SELDI-TOF mass spectrometry." BioTechniques 36(1): 32-34.

Peng et al., (2011). "Nanopore-based DNA sequencing and DNA motion control." Nanopores: Sensing and Fundamental Biological Interactions 11: 255-286.

Huang et al., (2010). "Identifying single bases in a DNA oligomer with electron tunneling." Nature Nanotechnology 5: 868-873.

Lindsay et al., (2010). "Recognition Tunneling." Nanotechnology 21: 262001-262013.

Lawson et al., (2006). "Transport in Molecular Junctions with different metallic contacts." Physical Review B 74: 125401.

Chang et al., (2011). "Gap Distance and Interactions in a Molecular Tunnel Junction." J. Am Chem Soc 133: 14267-14269.

Hempel, (2002). "An orientation to Edman chemistry." Modern Protein Chemistry 5: 103-122.

Chang et al., (2012). "Chemical Recognition and Binding Kinetics in a Functionalized Tunnel Junction." Nanotechnology 23: 235101.

Chang et al., (2011). "LIBSVM: a library for support vector machines." ACM Transactions on Intelligent Systems and Technology 2(3) 27:1-27:27.

Chen et al., (2007). "Subfemtomole level protein sequencing by Edman degradation carried out in a microfluidic chip." Chem. Commun. 24: 2488-2490.

Chen et al., (2007). "Optimization of microfabricated nanoliter-scale solid-phase extraction device for detection of gel-separated proteins in low abundance by matrix assisted laser desorption/ionization mass spectrometry." Rapid Communications in Mass Spectrometry 21: 35-43.

Tuchband et al., (2012). "Insulated gold scanning tunneling microscopy probes for recognition tunneling in an aqueous environment." Rev. Sci. Instrum. 83: 015102.

Louwagie et al., (2012). "Introducing AAA-MS, a Rapid and Sensitive Method for Amino Acid Analysis Using Isotope Dilution and High-Resolution Mass Spectrometry." J. Proteome Res. 11: 3929-3936.

Yan-Fei et al., (2007). "Development of C-Terminal Sequencing Analysis Protein and Peptide." Chin. J. Anal. Chem. 35: 1820-1826.

Baker et al., (2010). "An LC-IMS-MS Platform Providing Increased Dynamic Range for High-Throughput Proteomic Studies." J. Proteome Res. 9: 997-1006.

Held et al., (2011). "Quantitative urine amino acid analysis using liquid chromatography tandem mass spectrometry and aTRAQ reagents." J. Chromatography B 879: 2695-2703.

Selman et al., (2010). "Immunoglobulin G Glycopeptide Profiling by Matrix-Assisted Laser Desorption Ionization Fourier Transform Ion Cyclotron Resonance Mass Spectrometry." Anal. Chem. 82: 1073-1081.

Addona et al., (2009). "Multi-site assessment of the precision and reproducibility of multiple reaction monitoring-based measurements of proteins in plasma." Nature Biotechnology 27: 633-641.

Perkel, (2011). "The Human Proteome Project Takes Shape Down Under." BioTechniques 50(3): 149-155.

Hanash, (2003). "Disease proteomics." Nature 422: 226-232.

James, (1997). "Protein identification in the post-genome era: the rapid rise of proteomics." Quarterly Reviews of Biophysics 30(4): 279-331.

Anderson et al., (1998). "Proteome and proteomics: New technologies, new concepts, and new words." Electrophoresis 19: 1853-1861.

Uhlen et al., (2005). "Antibody-based Proteomics for Human Tissue Profiling." Molecular & Cellular Proteomics 4(4): 384-393.

Anderson et al., (2002). "The Human Plasma Proteome: History, Character, and Diagnostic Prospects." Molecular & Cellular Proteomics 1: 845-867.

Sanglier et al., (2003). "Comparative ESI-MS Study of 2.2 MDa Native Hemocyanins from Deep-Sea and Shore Crabs: From Protein Oligomeric State to Biotope." J. Am. Soc. Mass Spectrom. 14: 419-429.

Covey et al., (2010). "ESI, APCI, and Maldi A Comparison of the Central Analytical Figures of Metri: Sensitivity, Reproducibility, and Speed." Electrospray and MALDI Mass Spectrometry: Fundamentals, Instrumentation, Practicalities, and Biological Applications 13: 443-490.

Yates et al., (2009). "Proteomics by Mass Spectrometry: Approaches, Advances, and Applications." Annu. Rev. Biomed. Eng. 11: 49-79.

Thakur et al., (2011). "Deep and Highly Sensitive Proteome Coverage by LC-MS/MS Without Prefractionation." Molecular & Cellular Proteomics 10: M110.003699-1-M110.003699-9.

Zhou et al., (2012). "Advancements in Top-Down Proteomics." Anal. Chem. 84: 720-734.

Tran et al., (2011). "Mapping intact protein isoforms in discovery mode using top-down proteomics." Nature 480: 254-258.

Yang et al., (2008). "Preferential Dimethylation of Histone H4 Lysine 20 by Suv4-20." J. Biol. Chem. 283: 12085-12092.

Cannon et al., (2010). "High-Throughput Middle-Down Analysis Using an Orbitrap." Journal of Proteome Research 9: 3886-3890.

Wu et al., (2012). "A protease for 'middle-down' proteomics." Nature methods 9(8) 822-824.

Bandeira et al., (2008). "Beyond Edman Degradation: Automated de novo protein sequencing of monoclonal antibodies." Nature Biotechnology 26: 1336-1338.

Takulapalli et al., (2012). "High Density Diffusion-Free Nanowell Arrays." J. Proteome Res. 11(8): 4382-4391.

Huang et al., (2010). "Protein microarray: A key approach of proteomics." Front. Biol. 5(4): 331-338.

(56) References Cited

OTHER PUBLICATIONS

Gold et al., (2010). "Aptamer-Based Multiplexed Proteomic Technology for Biomarker Discovery." PLoS One 5(12): e15004.

Jacobs et al., (2004). "Utilizing Human Blood Plasma for Proteomic Biomarker Discovery." J. Proteome Res. 4: 1073-1085.

Huttenhain et al., (2012). "Reproducible Quantification of Cancer-Associated Proteins in Body Fluids Using Targeted Proteomics." Sci. Transl. Med. 4: 142ra94.

Westermann et al., (2012). "Dual RNA-seq of pathogen and host." Nat. Rev. Microbiol. 10: 618-630.

Liang et al., (2012). "Synthesis, Physicochemical Properties, and Hydrogen Bonding of 4(5)-Substituted-1H-imidazole-2-carboxamide, a Potential Universal Reader for DNA Sequencing by Recognition Tunneling." Chemistry—A European Journal 18(19): 5998-6007.

Venkatesan et al., (2011). "Nanopore sensors for nucleic acid analysis." Nature Nanotechnology 6: 615-624.

Yusko et al., (2011). "Nanopore Recording to quantify activity-related properties of proteins." Nanopores: sensing and fundamental biological interactions 9: 203-225.

Sutherland et al., (2004). "Structure of Peptides Investigated by Nanopore Analysis." Nano Letters 4(7): 1273-1277.

Stefureac et al., (2006). "Transport of α-Helical Peptides through α-Hemolysin and Aerolysin Pores." Biochemistry 45(30): 9172-9179.

Stefureac et al., (2012). "Modulation of the translocation of peptides through nanopores by the application of an AC electric field." Chem. Commun. (Camb) 48(13): 1928-1930.

Zhao et al., (2009). "Real-Time Monitoring of Peptide Cleavage Using a Nanopore Probe." J. Am. Chem. Soc. 131: 6324-6325.

Kang et al., (2006). "Stochastic Detection of Enantiomers." J. Am. Chem. Soc. 128, 10684-10685.

Astier et al., (2006). "Toward Single Molecule DNA Sequencing: Direct Identification of Ribonucleoside and Deoxyribonucleoside 5'-Monophosphates by Using an Engineered Protein Nanopore Equipped with a Molecular Adapter." J. Am. Chem. Soc. 128: 1705-1710.

Clarke et al., (2009). "Continuous base identification for single-molecule nanopore DNA sequencing." Nature Nanotechnology 4: 265-270.

Gao et al., (2009). "A Simple Method of Creating a Nanopore-Terminated Probe for Single-Molecule Enantiomer Discrimination." Anal. Chem. 81: 80-86.

Boersma et al., (2012). "Real-Time Stochastic Detection of Multiple Neurotransmitters with a Protein Nanopore." ACSnano 6(6): 5304-5308.

* cited by examiner

FIG. 6

| Amino acid | Peak Current (pA) | Count rate (hr$^{-1}$) |
|---|---|---|
| Glycine | 29 | 562 |
| asparagine | 40 | 1043 |
| phenylalanine | 89 | 148 |

| Model | LogNormal | | |
|---|---|---|---|
| Equation | y=y0+ A1/(sqrt (2.*PI)*w*x)* exp( (3n(x/xc))*2/(2*w *2)) | | |
| Reduced Chi-Sqr | 10.29308 | | |
| Adj R-Square | 0.89785 | | |
| | | Value | Standard Error |
| Count | y0 | 1.23996 | 0.72728 |
| Count | xo | 0.0576 | 0.00132 |
| Count | w | 0.38896 | 0.02391 |
| Count | A | 1.45937 | 0.06541 |

| Model | TwoLogNormal (User) | | |
|---|---|---|---|
| Equation | y=y0+ A1/(sqrt(2.0*PI)*w1*x)*exp(-(in(x/xc1))^2/(2.0*w1^2))+ A2/(sqrt(2.0*PI)*w2*x)*exp(-(in(x/xc2))^2/(2.0*w2^2)) | | |
| Reduced Chi-Sqr | 34.75641 | | |
| Adj R-Square | 0.96634 | | |
| | | Value | Standard Error |
| B | y0 | 4.82214 | 1.55573 |
| B | xc1 | 0.03421 | 4.35333E-4 |
| B | w1 | 0.25203 | 0.01305 |
| B | A1 | 2.06397 | 0.10604 |
| B | xc2 | 0.06034 | 6.34345E-4 |
| B | w2 | 0.11067 | 0.01106 |
| B | A2 | 0.84752 | 0.08985 |

"V"=microfluidic valve

| Amino Acid | True Positive Rate (1 peak call) |
|---|---|
| argenine | 0.721 |
| L-asparagine | 0.782 |
| D-asparagine | 0.705 |
| glycine | 0.754 |
| sarcosine | 0.826 |
| isoleucine | 0.714 |
| leucine | 0.776 |

SYSTEMS, APPARATUSES AND METHODS FOR READING AN AMINO ACID SEQUENCE

RELATED APPLICATIONS

This application is a U.S. national stage application of International Application No. PCT/US2013/024130, which was filed on Jan. 31, 2013 which claims benefit under 35 USC 119(e) of U.S. provisional patent application Nos. 61/593,552, filed Feb. 1, 2012, and entitled, "Apparatus And Method For Reading Amino Acid Sequence," and 61/647,847, filed May 16, 2012 of the same title. Each of these disclosures is herein incorporated by reference in its entirety.

STATEMENT REGARDING FEDERALLY SPONSORED RESEARCH & DEVELOPMENT

This invention was made with government support under grant R01 HG006323 awarded by the National Institutes of Health. The government has certain rights in the invention.

FIELD OF THE DISCLOSURE

Embodiments of the present disclosure relate to amino acid, peptide and protein, sequencing and identification, by means of, for example, electronic detection of individual amino acids or small peptides.

BACKGROUND OF THE DISCLOSURE

The human proteome, which is encoded by just some 25,000 genes, consists of millions of proteins variants, due to RNA splicing, post translational modifications (PTM), somatic DNA rearrangements, and single nucleotide polymorphisms (SNP). Despite the widespread interest in whole genome sequencing, the genome is largely fixed. While sequencing of mRNA is more informative, giving an average picture of the levels of gene expression, it yields little of post-translational modifications that generate the millions of proteins from just thousands of genes. There is a need of a massively parallel method to read human proteomes with high throughput and low cost. In contrast to the human genome in which DNA exists as diploid, the proteome has a wide dynamic range, for example the abundance of proteins in human plasma spans more than 10 orders of magnitude. Some proteins are expressed in a low quantity. Proteomics has no tool equivalent to the polymerase chain reaction (PCR) for protein sample amplification. There is no cost effective way to faithfully reproduce a protein population from a source. Thus, protein analysis must be carried out by extracting materials from samples removed from humans in some quantity.

There have been remarkable advances in sample preparation, and sequencing techniques, most notably based on mass spectroscopy as a proteomic tool. However, mass-spectrometers are large, costly machines. Their size is dictated by the need for very high mass resolution to obtain accurate identification of the amino acid components (and even then, readout is complicated by isobaric amino acids). Accordingly, there is a need for an alternative method for identifying amino acids, particularly in small quantities, and ideally at the single-molecule level.

In a series of earlier disclosures, WO2009/117522A2, WO 2010/042514A1, WO 2009/117517, WO2008/124706A2, US2010/0084276A1, and US2012/0288948, each of which is incorporated herein by reference, a system was disclosed where nucleic acid bases could be read by using the electron tunneling current signals generated as the nucleobases pass through a tunnel gap functionalized with adaptor molecules. A demonstration of the ability of this system to read individual bases embedded in a polymer was given by Huang et al.[1] This method is referred to as "Recognition Tunneling" (RT).[2] It was earlier recognized in these previous disclosures that, because the method is purely physical, in that it did not rely on the reactions of a DNA polymerase or ligase, any chemical residue should be able to be recognized provided that it generates a distinctive tunneling current signal.

Yet another problem in determining the human proteome arises because of the stereochemistry of amino acids. Amino acids can exist in two forms ("enantiomers") that are mirror images of each other. Nature has chosen the so called "L" (for left-handed) form in general, but the presence of "D" (for dextro or right handed) amino acids is an important biomarker for diseases such as ALS or schizophrenia. Since these enantiomers are isobaric, they cannot be sensed by mass spectroscopy, so large amounts of additional sample are needed for optical identification. Furthermore, control of optical isomers is one of the most difficult problems in chemical synthesis and separation. Since the isomers are chemically identical, it is very hard to extract pure samples of one isomer or the other. Thus, a method to read the relative concentrations of isomers from very small amounts of sample would represent a major advance. Present, optical techniques require large amounts of sample. In addition, it would be advantageous to provide a simple method for reading the identity of optical isomers at the single molecule level.

SUMMARY OF THE DISCLOSURE

Accordingly, it is an object of some of the embodiments of the present disclosure to provide a method for sequencing and/or identifying amino acid molecules. It is another objective of some of the embodiments of the present disclosure to provide a method to read sequences of proteins and peptides. It is yet another objective of some embodiments to detect enantiomers at the single molecule level. Accordingly, it is an object of some of the embodiments of the present disclosure to provide a method for sequencing and/or identifying at least one protein, peptide, amino acid and/or modified amino acid.

These and other objectives are achieved by at least some of the embodiments of the present disclosure. In some embodiments, an apparatus is provided which includes a plurality of electrodes which are closely spaced, where at least one electrode (and, in some embodiments preferably more than one electrode) is functionalized with molecules that bind transiently to the analyte target. In some embodiments, the apparatus includes two such electrodes where each is functionalized with such molecules. In some embodiments, at least two of the electrodes enclose a space into which an analyte can be drawn, by diffusion, electrophoresis, dielectrophoresis and/or electro-osmosis (for example). Accordingly, in some embodiments, on binding an analyte to the recognition molecules, a series of current spikes signal the identity of the molecule upon a bias being applied between the electrodes. In some embodiments, the small analyte molecules are generated from a parent protein by placing the electrode(s) in close proximity to a bead containing proteases that digest the protein to be analyzed.

According to some of the embodiments of the present disclosure, a computer system is additionally included, as well as associated software for operating such a computer and operating embodiments for identifying and, in some embodiments, sequencing/identifying proteins and/or peptides, analyzing amino acids, as detailed herein.

According to some embodiments, an apparatus for identifying and/or sequencing at least one protein, peptide, amino acid and/or modified amino acid is provided, where the apparatus includes a plurality of electrodes, at least a first electrode of the plurality of the electrodes being functionalized with a molecular adaptor that is strongly bonded to at least the first electrode and that forms non-covalent bonds with an amino acid, voltage means (e.g., a voltage biasing device, which may comprise a power supply) for applying a voltage between the first electrode and a second electrode of the plurality of electrodes, where the first and second electrodes are arranged such that a gap is produced between them, and current data monitoring means (e.g., a current measuring device) for monitoring current passing between the first and second electrodes upon a solution containing at least one protein, peptide, amino acid and/or modified amino acid being passed in the gap established between the first and the second electrodes. In some embodiments, a database and processing means (e.g., a computer processor, which may also include a memory) may also be included where the database includes data associated with characteristic current signatures for a plurality of amino acids and amino acid derivatives, where the processing means has computer instructions operating thereon configured to compare the amino acid and the derivative signatures (which are contained in the database, for example) with the current data to determine the identity of the amino acid, peptide and/or protein. Moreover, the chirality of the amino acid may be determined from the current data.

In some embodiments, an assembly used in an apparatus for sequencing and/or identifying at least one protein, peptide, amino acid, and/or modified amino acid, may include a silicon substrate covered with a thin layer of dielectric between about 1 nm and about 100 nm in thickness, a window etched through the silicon substrate, a metal electrode layer deposited onto the dielectric layer which may comprise at least one of silver, gold, palladium or platinum between about 1 nm and about 10 nm in thickness, an adhesive layer of at least one of Ti or Cr of about 1 nm, a second layer of dielectric deposited onto the metal electrode layer comprising at least one of silicon nitride, silicon dioxide or hafnium oxide, the layer having a thickness of between about 1 nm and about 4 nm in thickness, a second metal electrode deposited on top of the second dielectric layer comprising at least one of silver, gold, palladium or platinum between about 1 nm and about 10 nm in thickness, a third layer of dielectric deposited on top of the apparatus and is formed to contact each pair of electrode planes at each apparatus, and a nanopore of between about 1 and 5 nm in diameter provided through the entire assembly.

In some embodiments, a method for sequencing/identifying at least one protein, peptide, amino acid, and/or modified amino acid is provided and may include one or more of the following steps: flowing a fluid containing at least one protein, peptide, amino acid, and/or modified amino acid in a gap provided between two closely spaced electrodes, where: at least one of the electrodes is functionalized with molecules that form transient, non-covalent, bonds with a target amino acid, and the target molecules diffuse freely into the gap from solution, and/or can be driven into the gap upon the gap spanning a nanopore through which fluid flows. Fluid flow may be accomplished via at least one of a pressure gradient, electroosmosis, dielectrophoresis and electrophoresis. Signals may be generated as the fluid flows through the gap which is representative of the at least one of protein, peptide and amino acid contained in the fluid. Additional steps may include determining the at least one of protein, peptide and amino acid based on the signals.

Determining the at least one of protein, peptide and amino acid may comprise determining at least one of: a width of signal spikes, a ratio of "on" to "off" time in a signal burst, a duration of a signal burst, a degree of clustering of the peaks, a flatness of the top of the spike of a signal, a frequency of the signal spikes, a rise and/or fall time of the signal spikes, and a shape of the signal spikes.

Some embodiments may include a computer system for sequencing/identifying at least one protein, peptide, amino acid, and/or modified amino acid which comprises a processor, where the processor includes computer instructions operating thereon for performing steps of a method for identifying and/or sequencing at least one protein, peptide, amino acid and/or modified according to any of the disclosed embodiments. Other related embodiments include a computer program for identifying and/or sequencing at least one protein, peptide, amino acid, and/or modified amino acid comprising computer instructions for performing such steps, as well as computer readable media (e.g., CD, DVD, flashdrive, and the like) containing such a program operable on a computer system.

In some embodiments, a molecular recognition apparatus is provided which may be configured to identify at least one portion of a target molecule. The apparatus may include a microfluidic channel containing first and second sensing electrodes, where the electrodes are separated from one another by a gap for receiving a target molecule, a first affinity element connected to the first electrode, and a second affinity element connected to the second electrode. When a portion of the target molecule is adjacent to the gap and completes a circuit between the electrodes, the device is configured to enable an electrical current to pass through the first electrode, the first affinity element, the portion of the target molecule, the second affinity element, and the second electrode.

The above-noted embodiments, and embodiments disclosed throughout this application, are merely examples of the many embodiments disclosed herein. Such embodiments further include embodiments which are similar to those set out above/below, but which may include less than the recited features, and others still, more than the recited features, thereof. Moreover, other embodiments include a combination of features of the embodiments exemplified above, below and throughout the application.

Some embodiments of the disclosure are further described in the following detailed description and included drawings.

BRIEF DESCRIPTION OF THE DRAWINGS

FIG. 6 illustrates peak currents (pA) and count rates from glycine, asparagine and phenylalanine at a gap conductance of 8 pS (I=4 pA, V=0.5V) produced by some embodiments of the present disclosure.

[1] Few of the background peaks are present at peak heights above 20 pA; data is accumulated over about 1 h (or about 1 count per minute).

Figure 9:
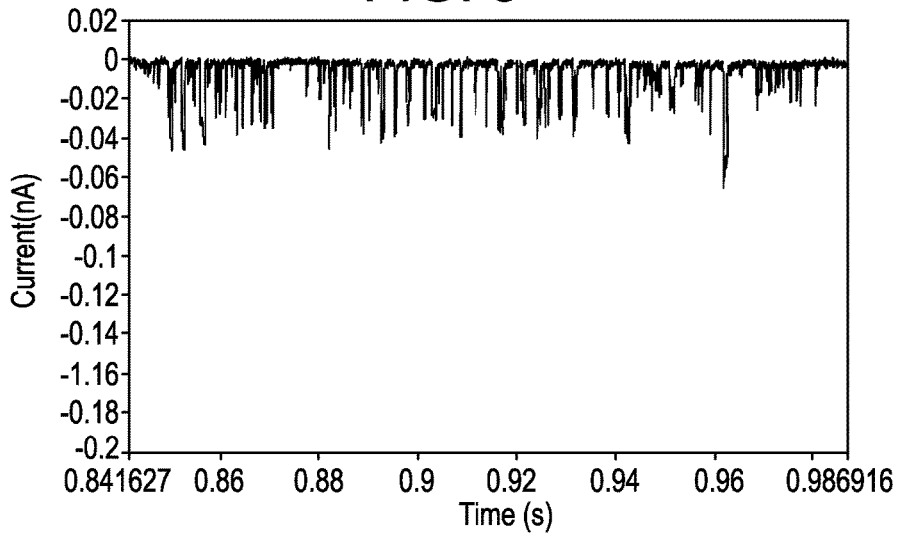

FIG. 9 illustrates signals from D-asparagine using gold electrodes at a bias of 0.8V and a tunnel current of 6 pA over a timescale of about 100 ms produced by some embodiments of the present disclosure.[FN2]

[2] Frequent spikes are observed, most of which greatly exceed the water background of 20 pA and occur at much higher frequency.

Figure 10:
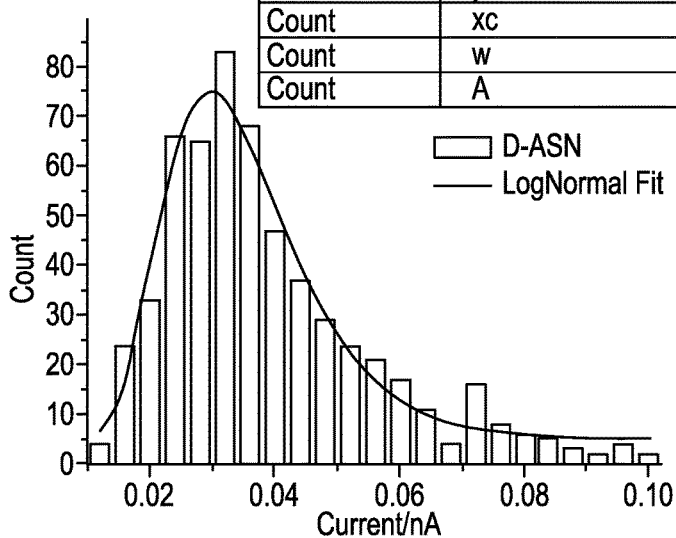

FIG. 10 illustrates a distribution of pulse heights from D asparagine using gold electrodes at a bias of 0.8V and a tunnel current of 6 pA produced by some embodiments of the present disclosure.[FN3]

[3] The peak of a log-normal distribution fit is 33.5 pA.

Figure 11:
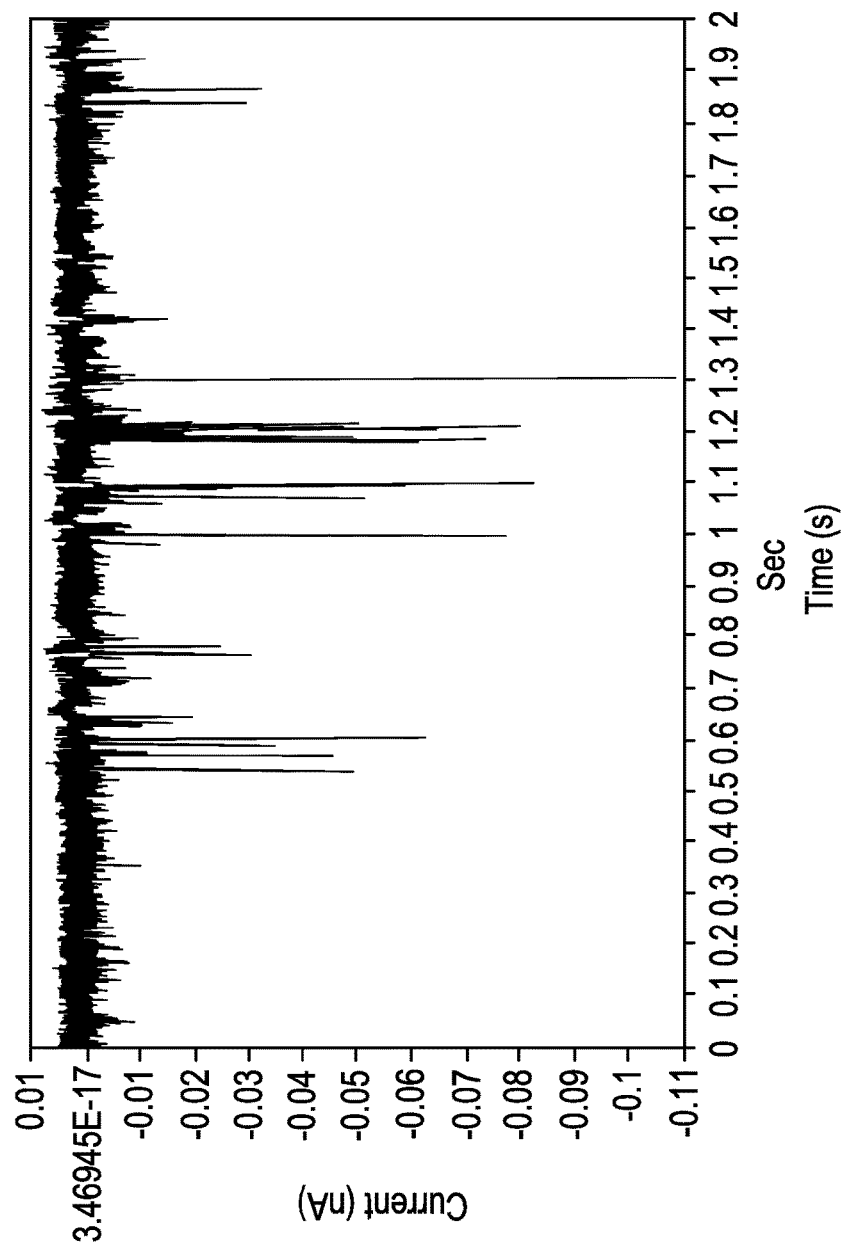

FIG. 11 illustrates typical signals from L-asparagine using gold electrodes at a bias of 0.8V and a tunnel current of 6 pA over a timescale of about 2 s produced by some embodiments of the present disclosure.

Figure 12:
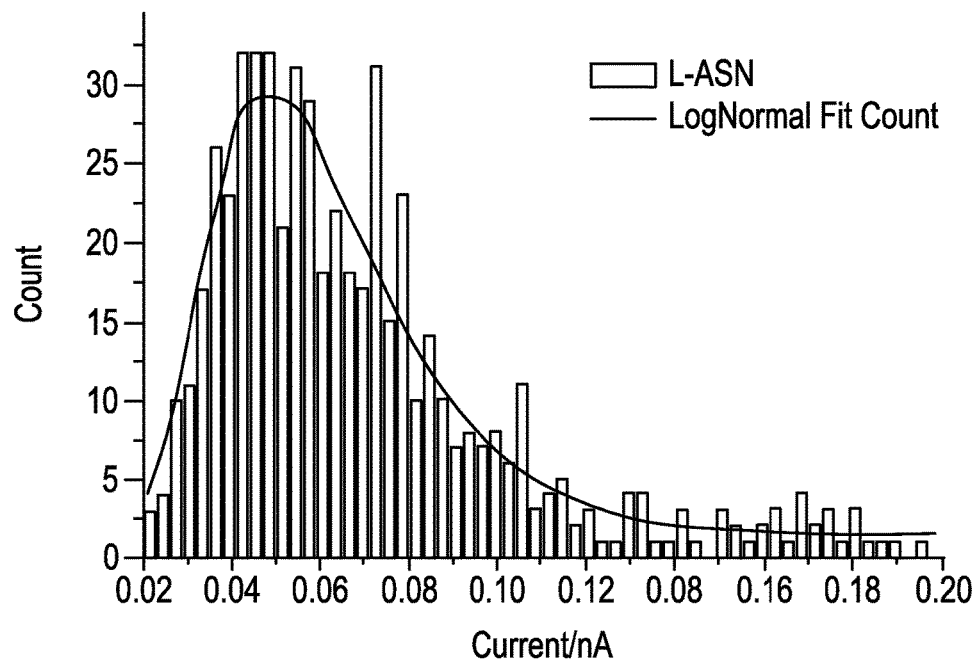

FIG. 12 illustrates a distribution of pulse heights from L-asparagine using gold electrodes at a bias of 0.8V and a tunnel current of 6 pA, with the peak of a log-normal distribution fit is 58 pA, produced by some embodiments of the present disclosure.

Figure 13:
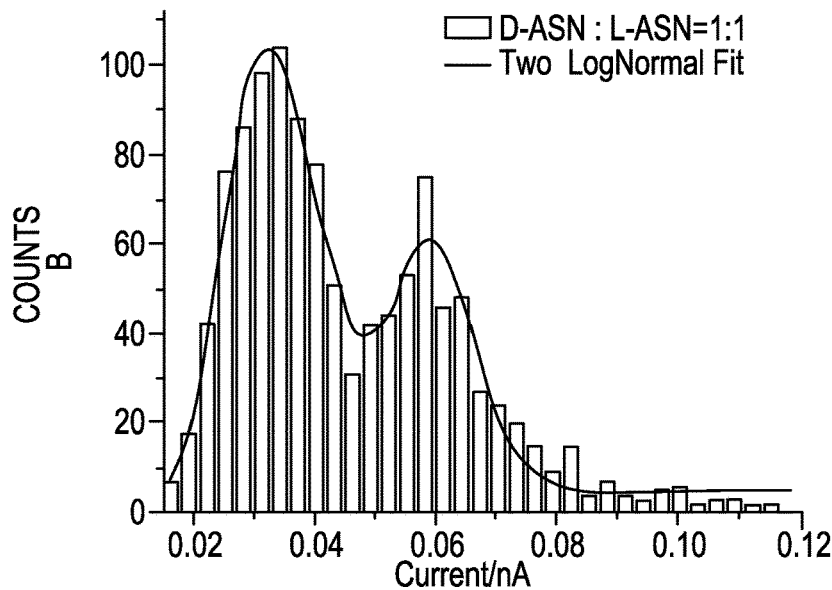

FIG. 13 illustrates a distribution of pulse heights from an equimolar mixture of D- and L-asparagine using gold electrodes at a bias of 0.8V and a tunnel current of 6 pA, produced by some embodiments of the present disclosure, where the distribution is fitted by two log-normal functions with peaks at 34 and 60 pA.

Figure 14:
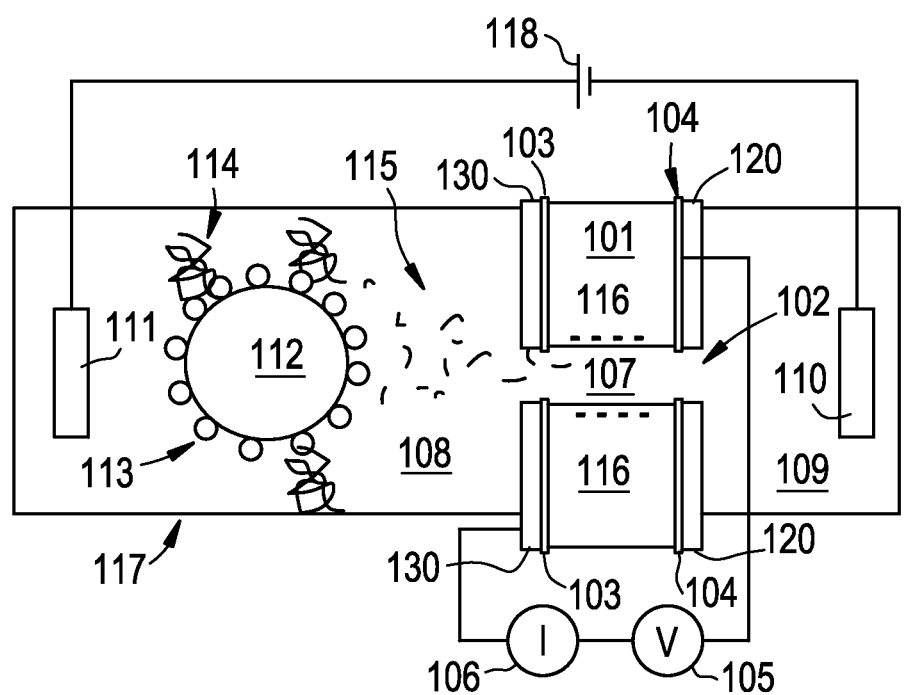

FIG. 14 illustrates an apparatus for protein, peptide, amino acid, and/or modified amino acid identification and/or sequencing according to some embodiments of the present disclosure.

Figure 15:
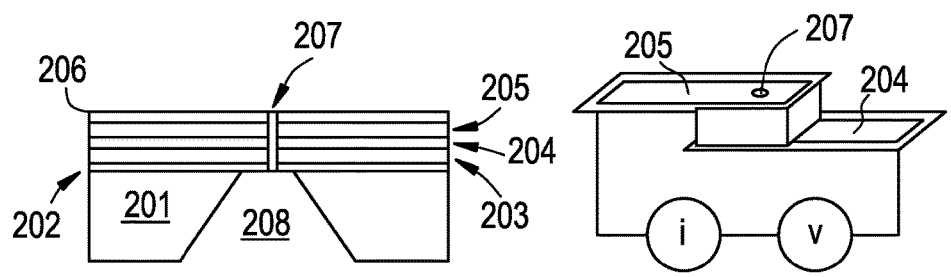

FIG. 15 illustrates the construction of nanopore apparatus articulated with electrodes according to some embodiments of the present disclosure.

Figure 16:
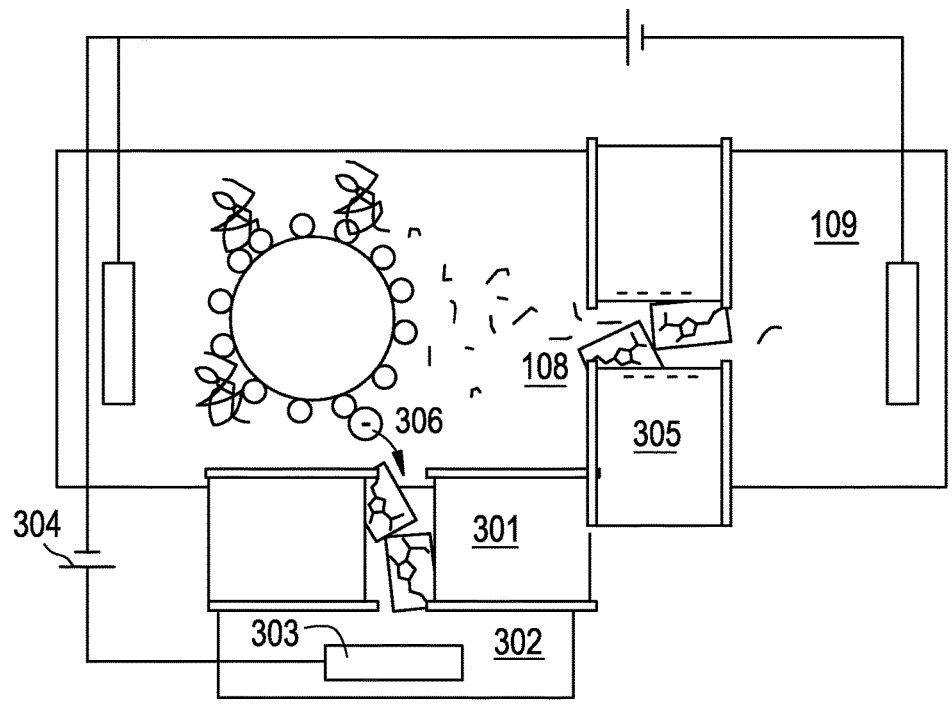

FIG. 16 illustrates an apparatus with a second nanopore and trans chamber biased for collecting negatively charged amino acids and peptide fragments according to some embodiments of the present disclosure.

Figure 17:
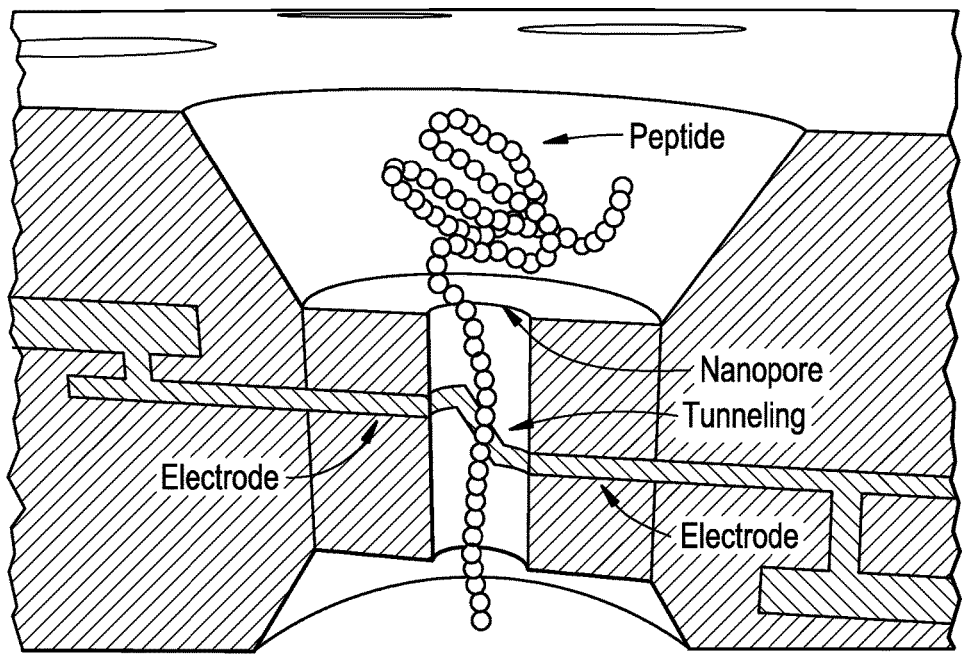

FIG. 17 is an illustration of peptide sequencing by directly tunneling reading of amino acid residues, according to some embodiments of the present disclosure.

Figure 18:
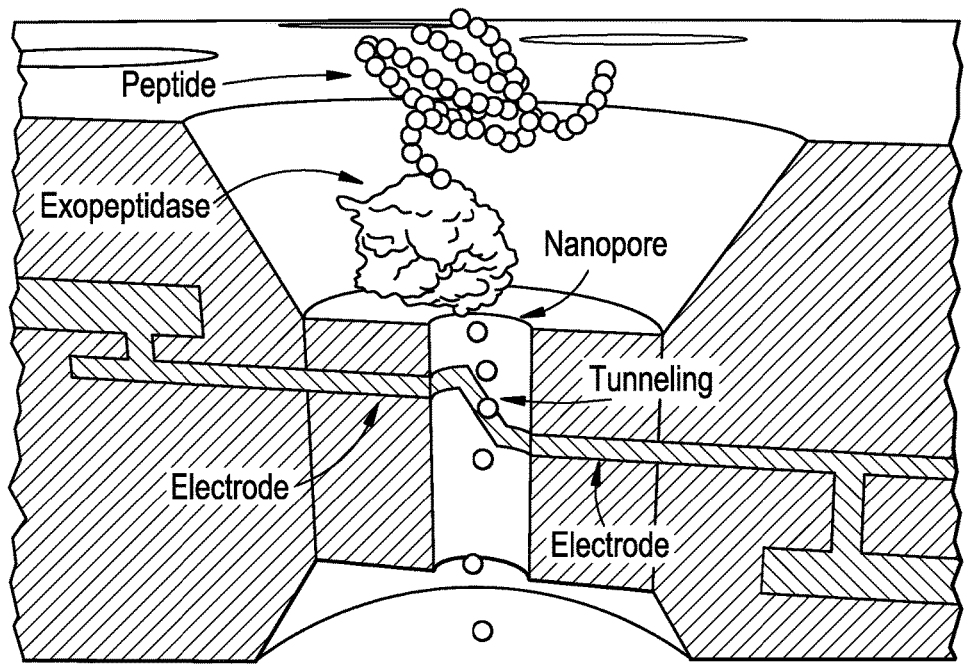

FIG. 18 is an illustration of peptide sequencing by enzymatically cleaving amino acids from a terminal of protein, according to some embodiments of the present disclosure.

Figure 19A:
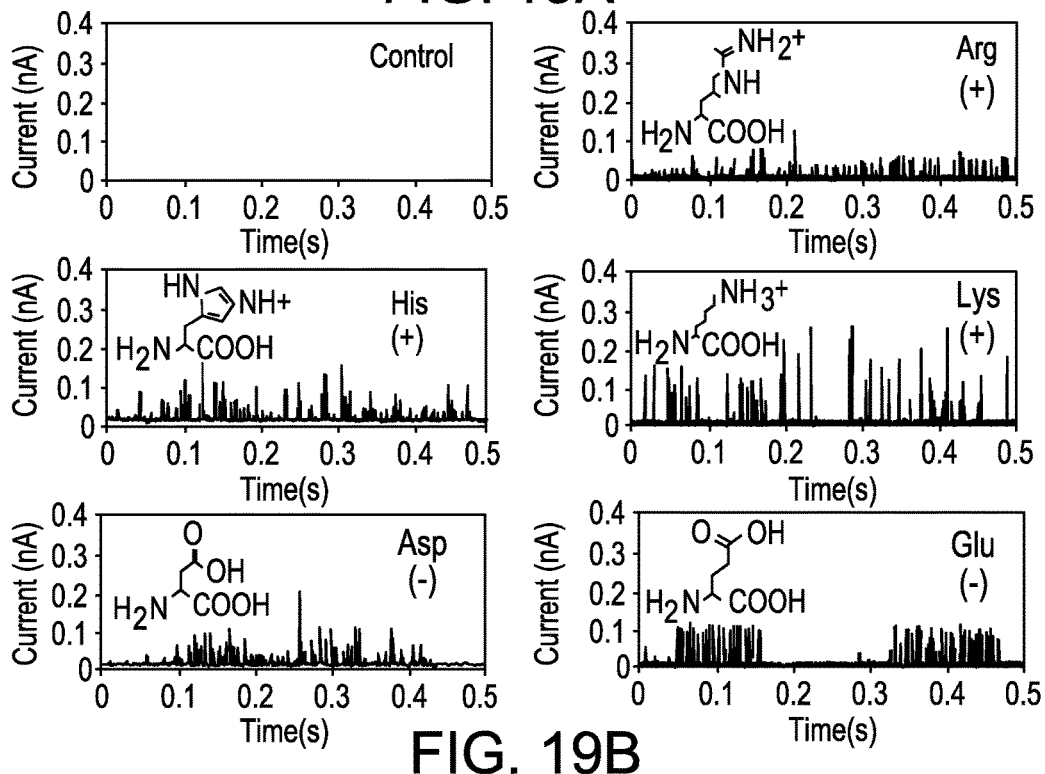
Figure 19B:
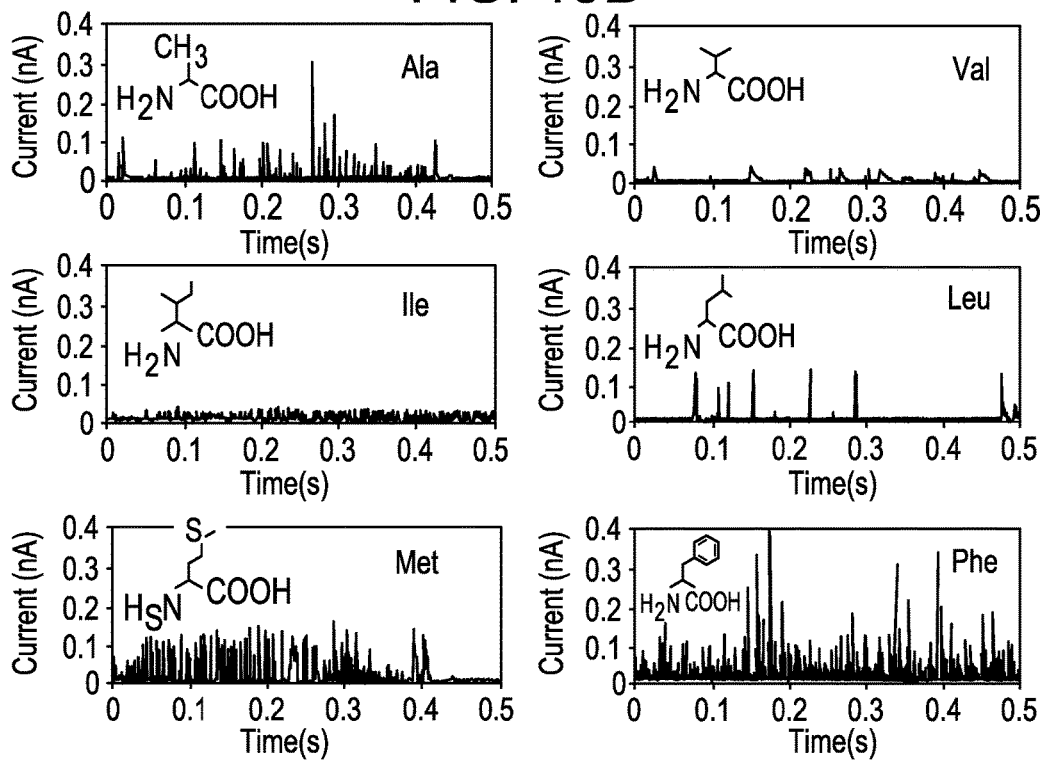
Figure 19C:
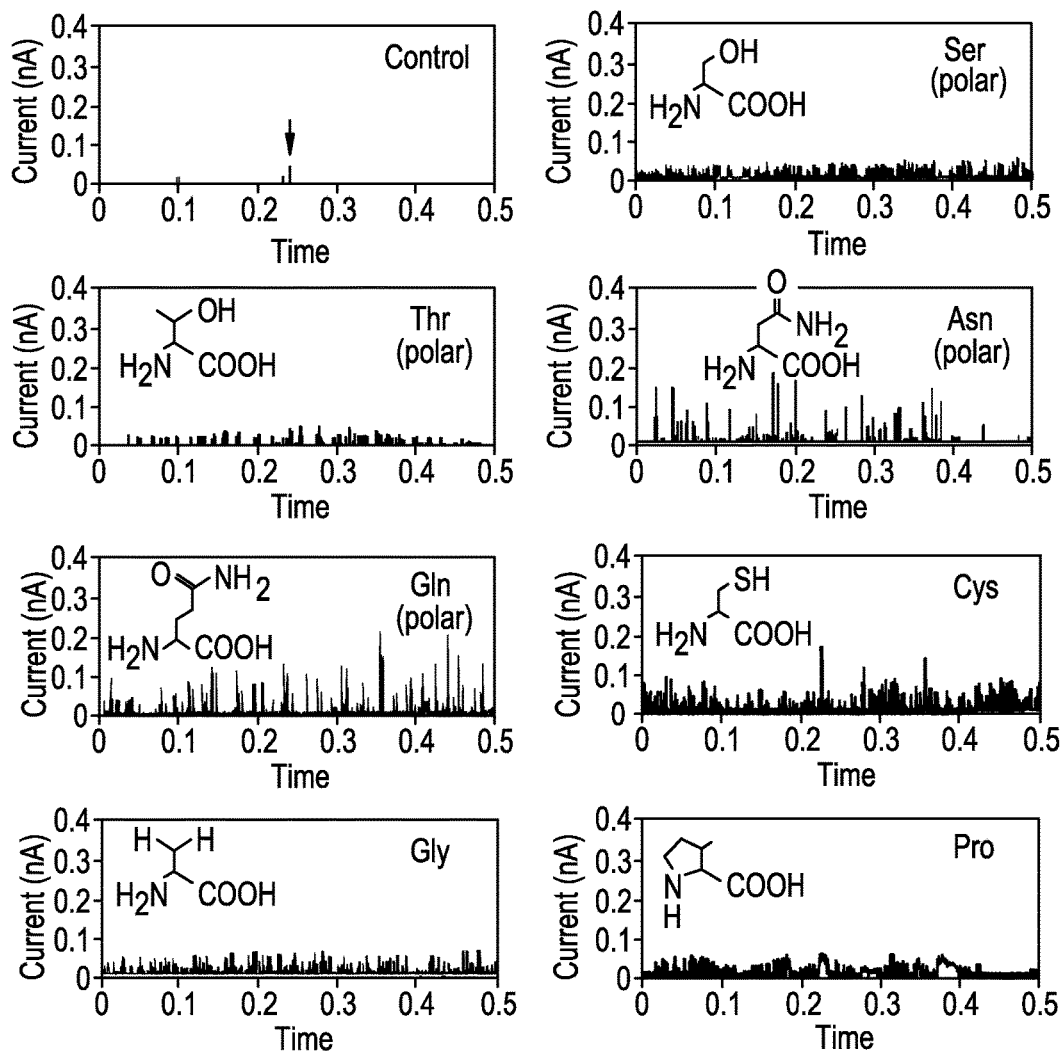

FIGS. 19A-C illustrate characteristic signal traces for 18 of the 20 amino acids together with two examples of control data (upper left panels in 19A and 19C) obtained with buffered electrolyte alone, with an apparatus according to some embodiments, the data being obtained using palladium electrodes and free of background signals produced by gold electrodes.

Figure 20A:
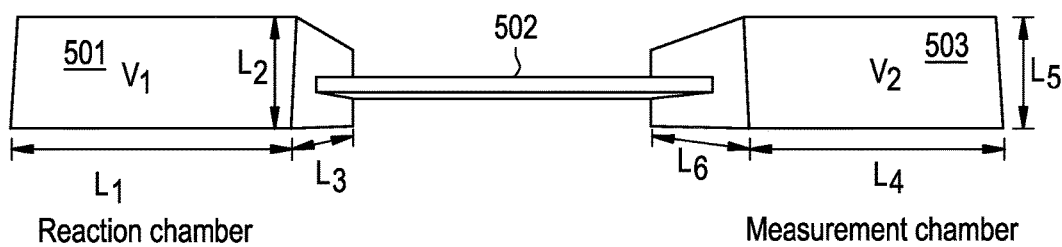

FIG. 20A illustrates a protein sequence reader apparatus without a nanopore according to some embodiments of the present disclosure.

Figure 20B:
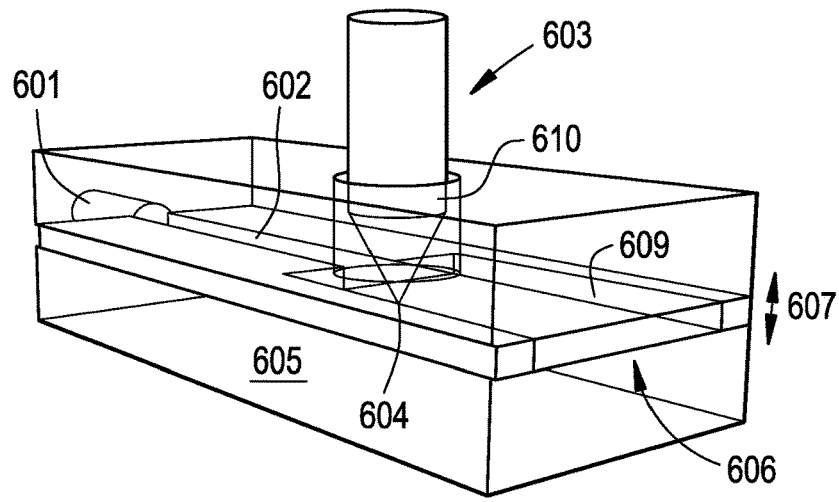

FIG. 20B illustrates a measurement cell apparatus having a nanoliter volume according to some embodiments of the present disclosure.

Figure 20C:
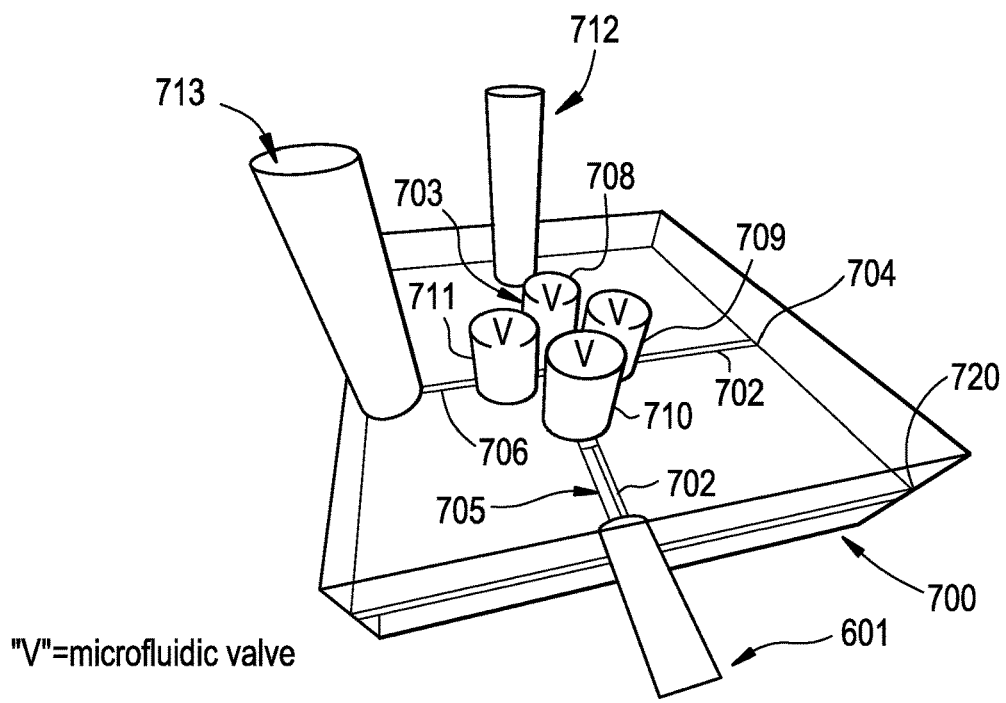

FIG. 20C illustrates a view of a nanoliter scale reaction system according to some embodiments of the present disclosure.

Figure 20D:
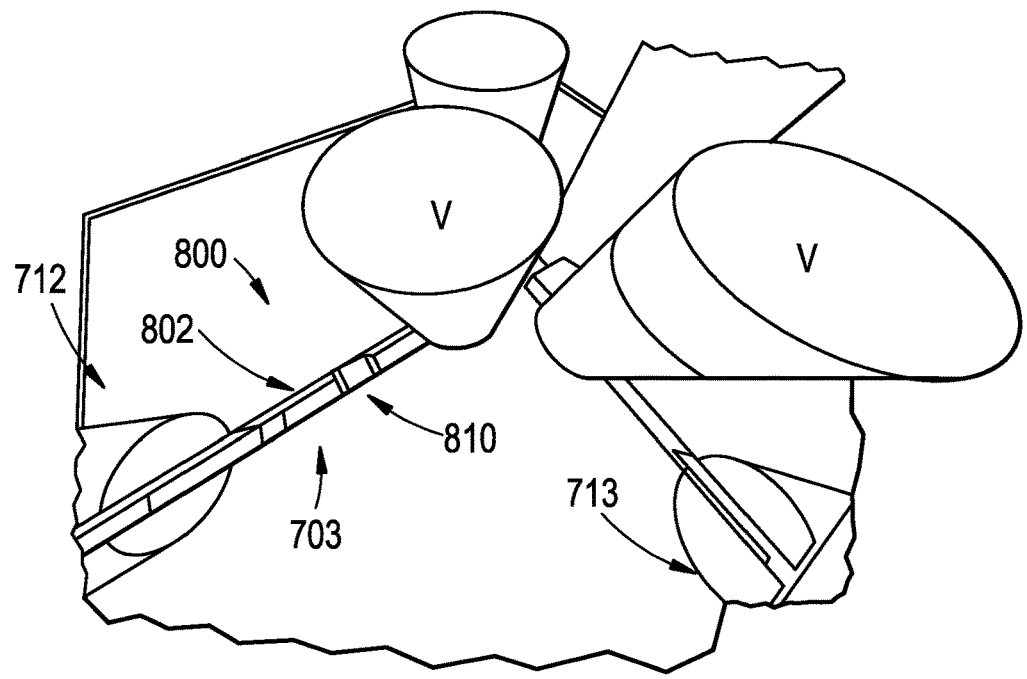

FIG. 20D illustrates a view down into the reaction chamber 703 of FIG. 20C.

Figure 20E:
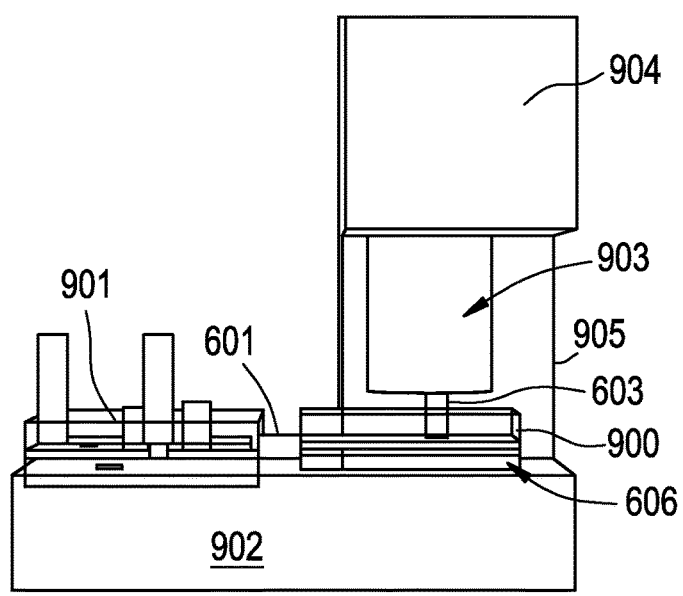

FIG. 20E illustrates a view of the overall assembly of the nanoliter scale reaction system according to some embodiments of the present disclosure.

Figure 21A:
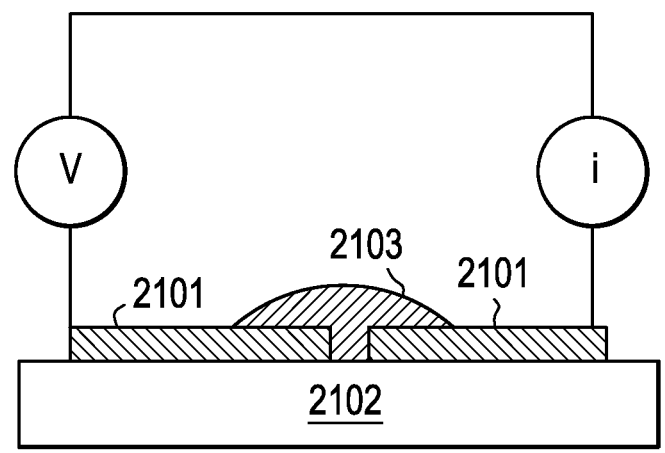

FIG. 21A illustrates a schematic view of a tunnel gap apparatus, according to some embodiments, created by cutting a palladium wire on a silicon nitride substrate with an electron beam, and the overall assembly of the nanoliter scale reaction system according to some embodiments of the present disclosure.

Figure 21B:
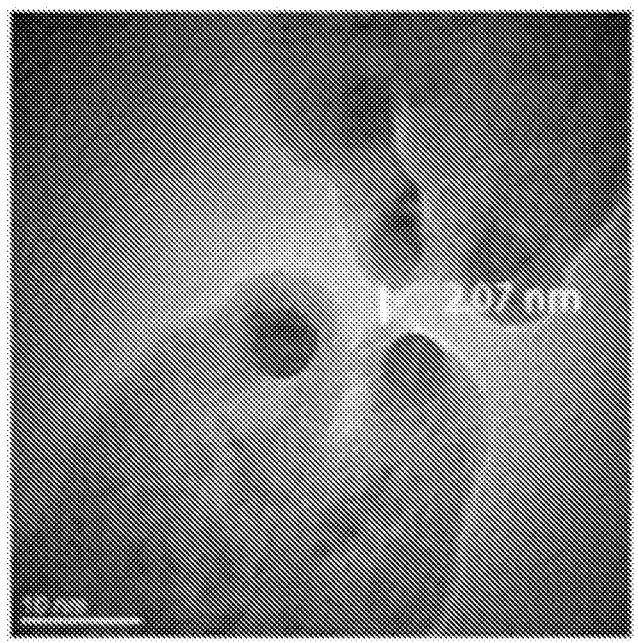

FIG. 21B is a TEM image of a tunnel gap, according to some embodiments, prior to functionalizing with imidazole carboxamide recognition molecules.

Figure 21C:
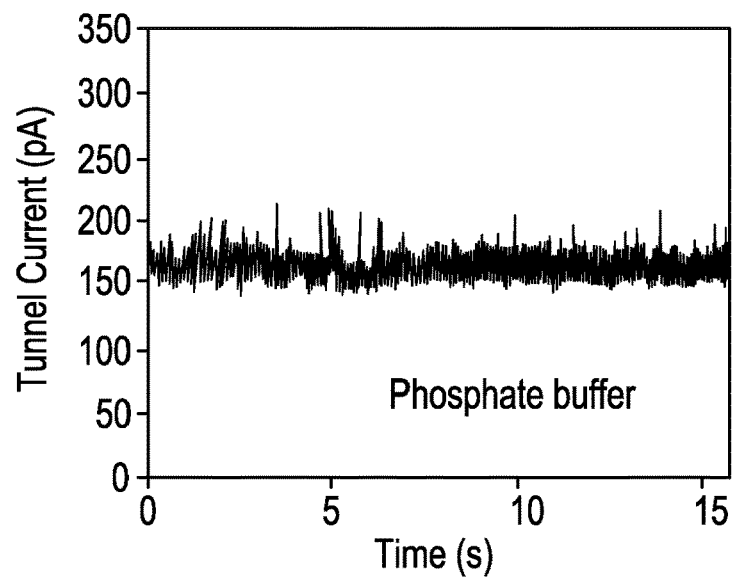

FIG. 21C is a graph illustrating the current signals produced with a phosphate buffer (pH7) using a sequencing device according to some embodiments of the present disclosure.

Figure 21D:
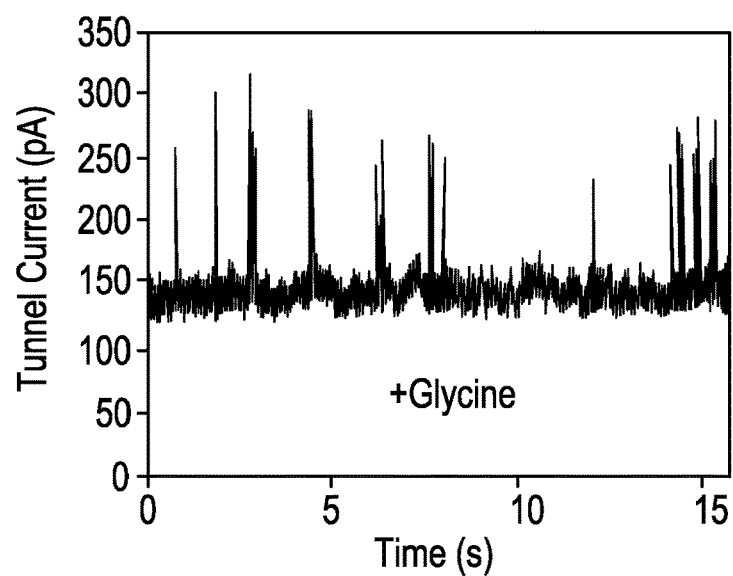

FIG. 21D is a graph illustrating the current signals produced with the sequencing device used in the signals generated in FIG. 21C, but after adding 100 micromolar glycine.

Figure 22A:
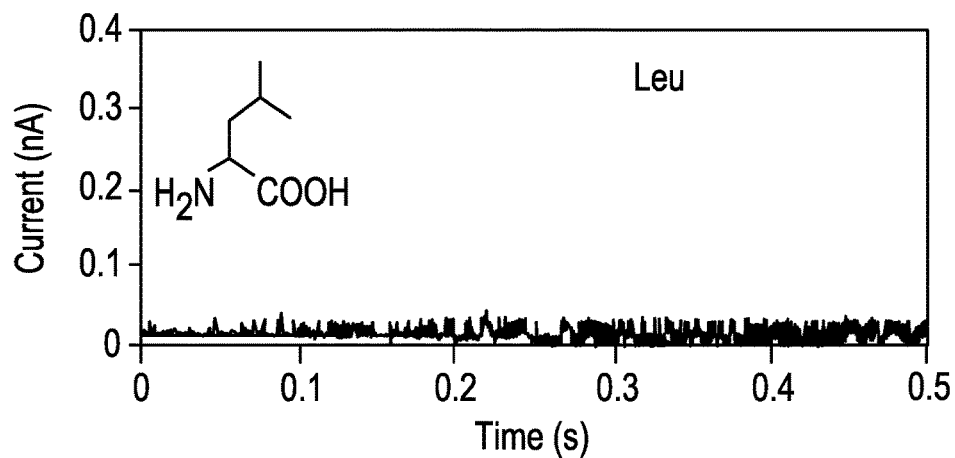

FIG. 22A is a graph illustrating current signals recorded of L-leucine in a sequencing system according to some embodiments of the present disclosure.

Figure 22B:
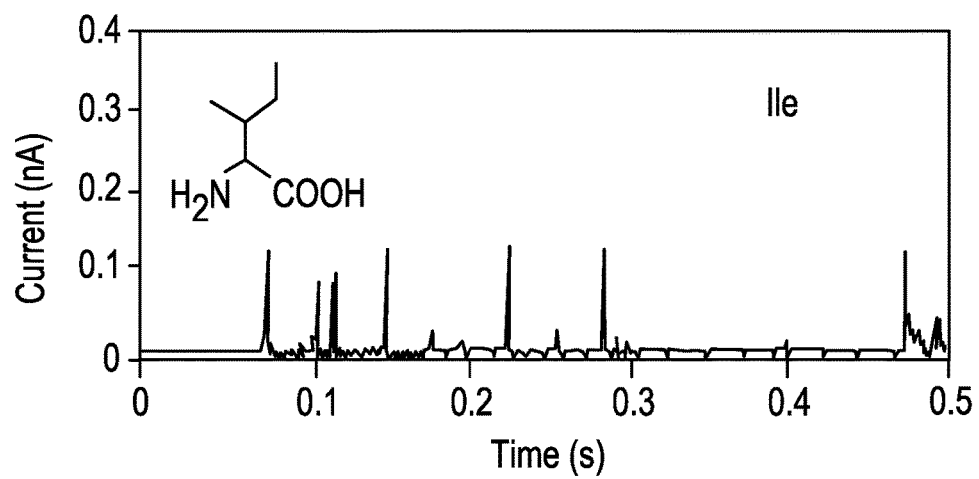

FIG. 22B is a graph illustrating current signals recorded of L-isolleucine in a sequencing system according to some embodiments of the present disclosure.

Figure 22C:
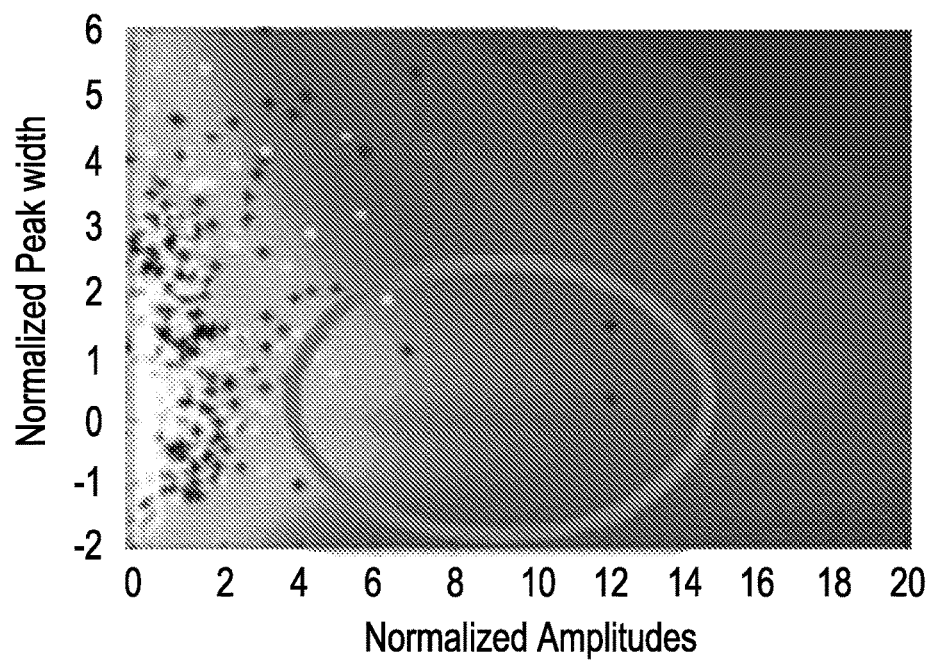

FIG. 22C is an image depicting the normalized peak width vs. normalized amplitudes of the signals from FIG. 22A.

Figure 22D:
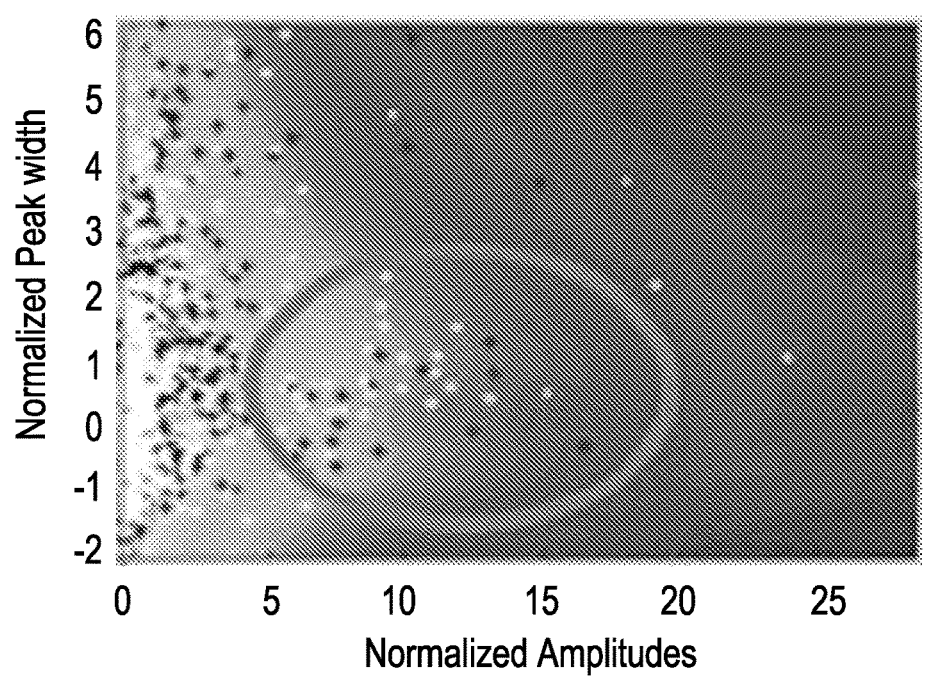

FIG. 22D is an image depicting the normalized peak width vs. normalized amplitudes of the signals from FIG. 22B.

Figure 22E:
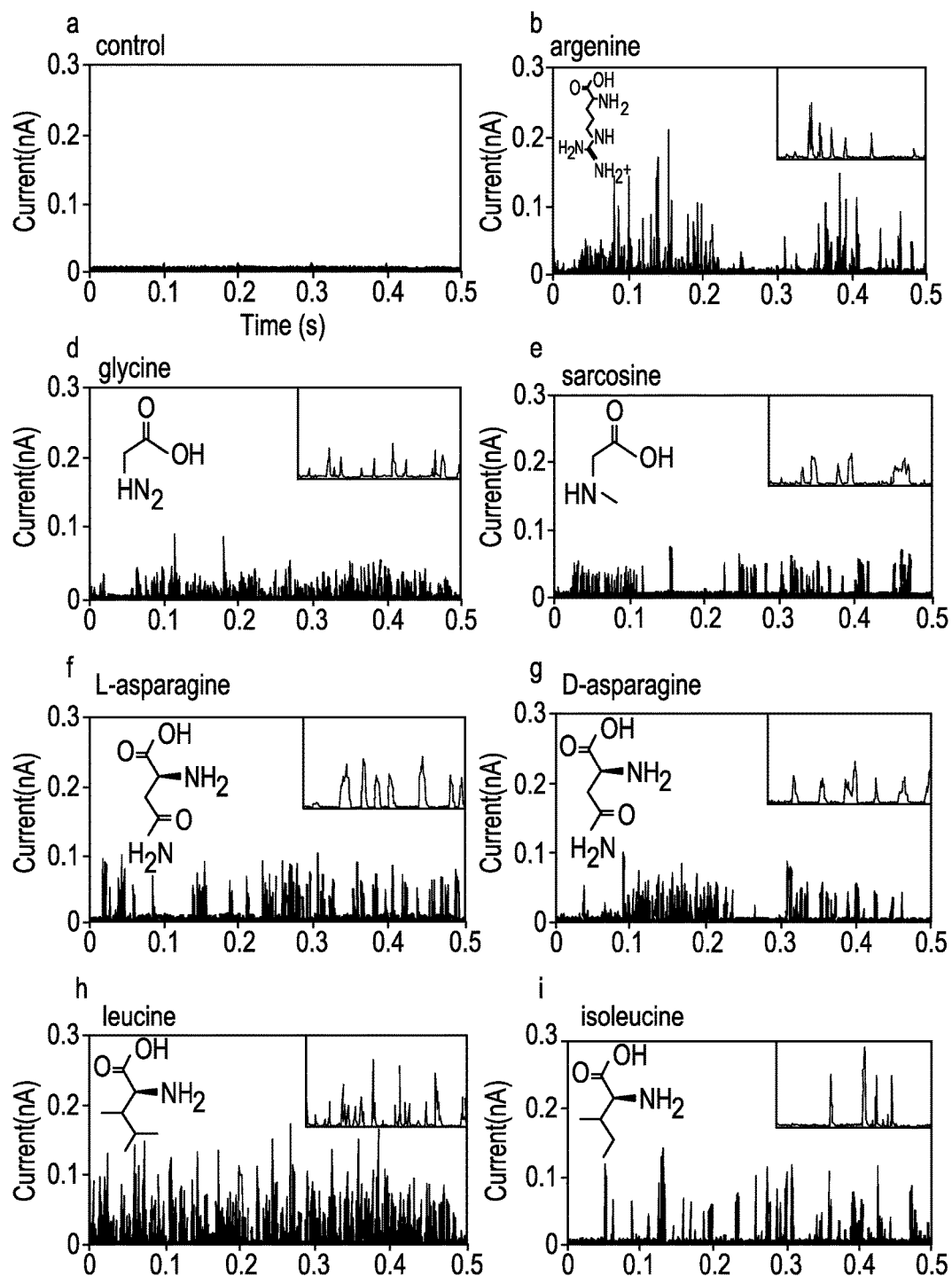

FIG. 22E shows typical spectra from a series of multiple repeated measurements on seven amino acids (as listed on the figure) according to some embodiments of the present disclosure (panels a-i). The insets show features at higher resolution (current scale 150 pA. time scale 20 ms). One of the analytes is sarcosine (methyl glycine, panel e) an example of a modified amino acid. Leakage current is controlled so that the tunnel gap is substantially is the same on repeated runs, and a covariance analysis is carried out to determine which signal parameters are consistent across the different experiments. These parameters were then used as input for support vector machine analysis.

Figures 22F, 23A:
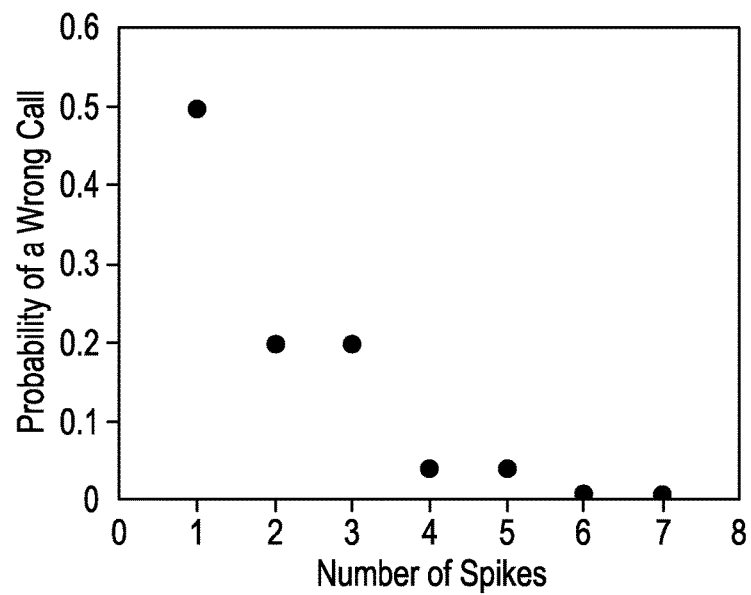

FIG. 22F is a Table summarizing true positive rate for identifying an amino acid based on a single peak in a data train after an analysis using the support vector machine, according to some embodiments of the present disclosure. The data is for a mixed pool of data for all seven amino acids listed.

FIG. 23A is a graph of predicted accuracy (i.e., fraction of wrong calls) of a sequencing system according to some embodiments of the present disclosure.

Figure 23B:
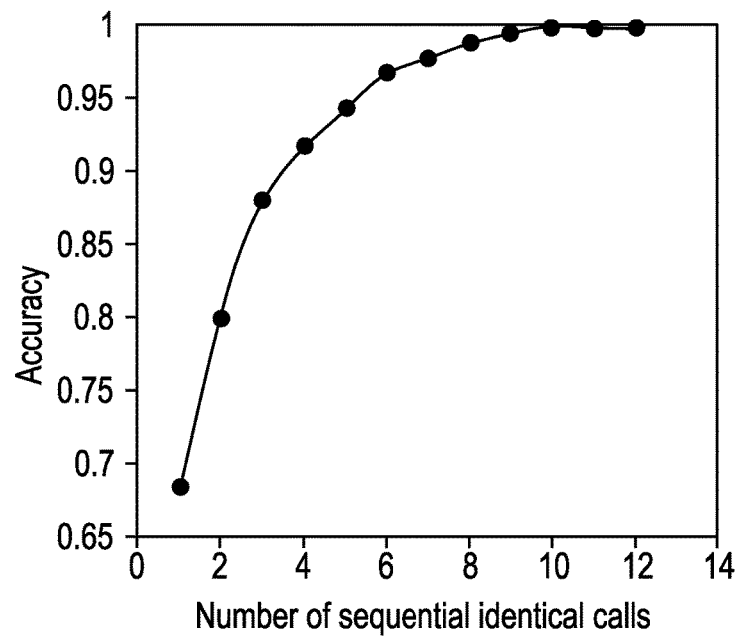

FIG. 23B shows the measured true positive rate obtained by requiring that a particular number of spikes make the same call sequentially, according to some embodiments of the present disclosure.

Figure 23C:
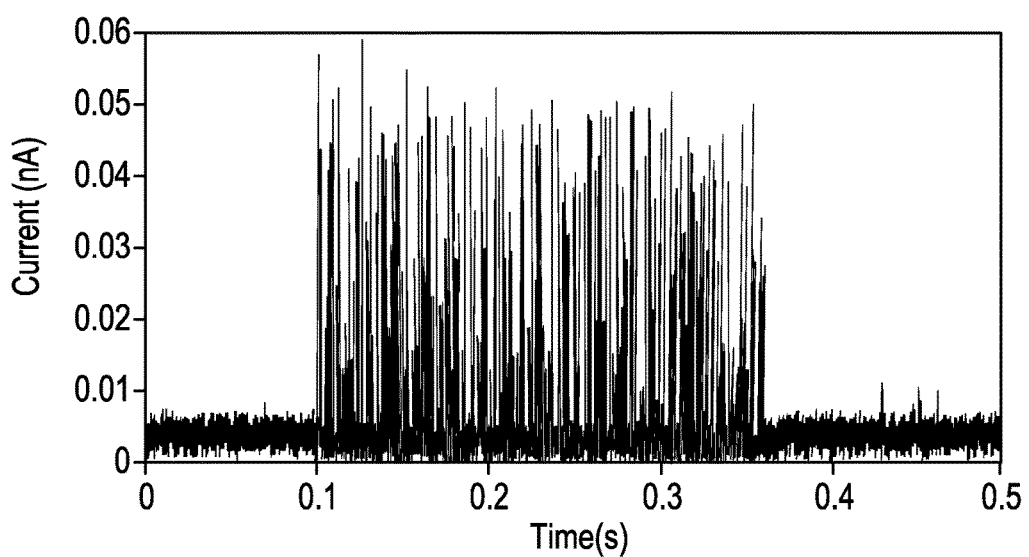

FIG. 23C shows a signal from a peptide consisting of three repeated amino acids (gky-gly-gly) showing that reads can be obtained from amino acid polymers according to some embodiments of the present disclosure.

Figure 24:
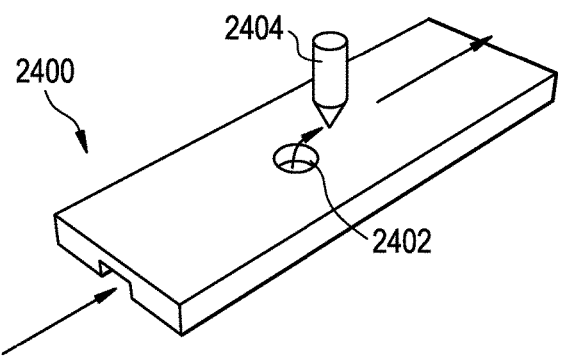

FIG. 24 is a perspective, schematic view of a sequencing system according to some embodiments, illustrating pressure injection (via, e.g., a pump, syringe, and the like) into the tunnel gap.

Figure 25:
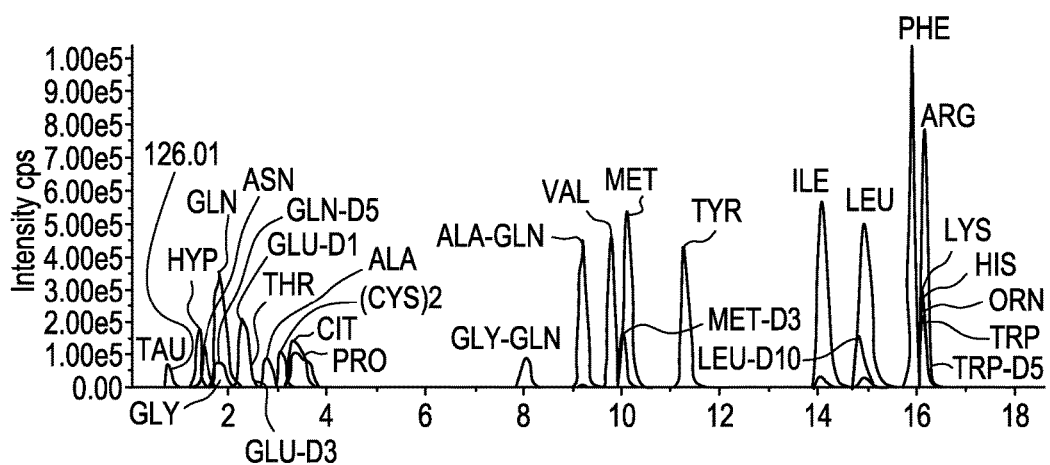

FIG. 25 is a graph of an HPLC chromatogram for 25 amino acids without derivatization.

Figures 26, 27:
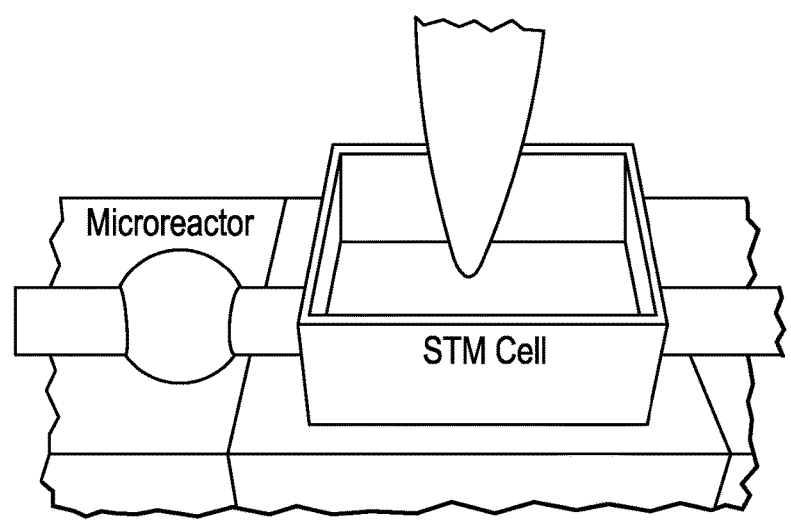

FIG. 26 is a perspective view of a micro-reactor coupled to an RT system through a microfluidics channel for determining sequences of peptides, according to some embodiments of the present disclosure.

FIG. 27 illustrates the sequencing a peptide by RT in combination with enzymatic hydrolysis according to some embodiments of the present disclosure.

Figure 28:
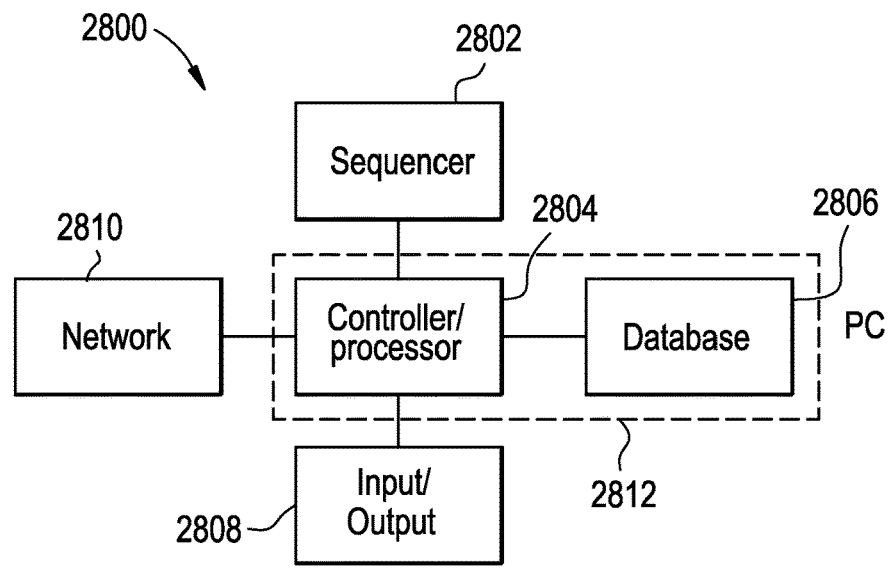

FIG. 28 is a block diagram of a sequencing system according to some embodiments of the present disclosure.

Figure 29:
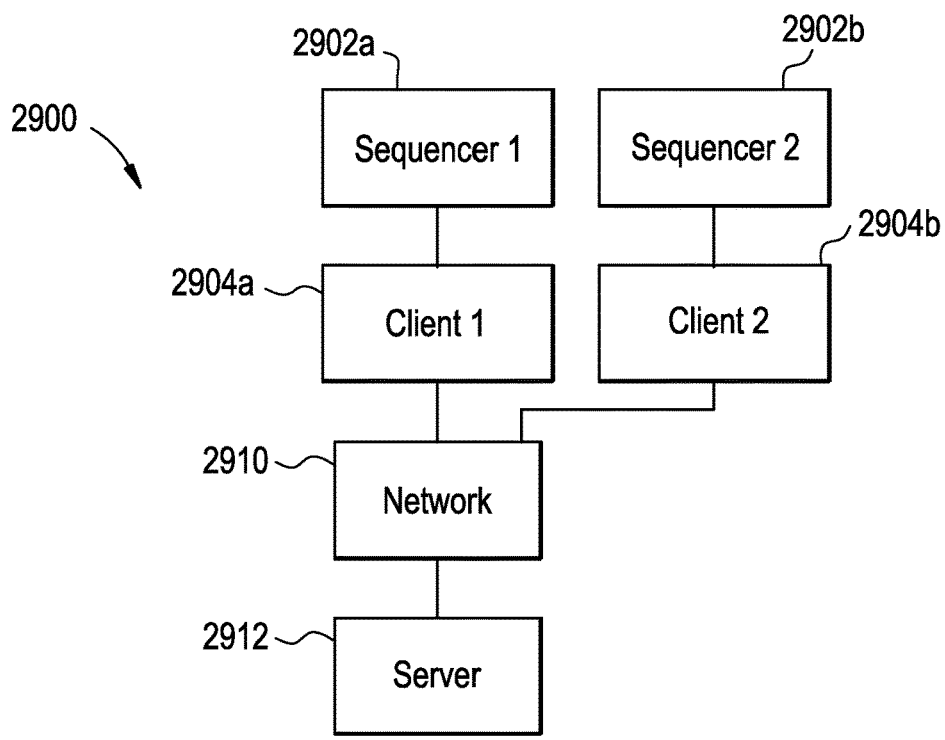

FIG. 29 is a block diagram of a sequencing system according to some embodiments of the present disclosure.

DETAILED DESCRIPTION

In some embodiments of the present disclosure, RT relies on passing an analyte between two closely spaced electrodes, each of which is functionalized with molecules that form transient, non-covalent, bonds with the target analyte. The target molecules may diffuse freely into the gap from solution, and/or they can be driven into the gap if the gap spans a nanopore through which fluid flows. Fluid can be made to flow through the gap by means of, for example, at least one of a pressure gradient electrophoresis, dielectrophoresis and electroosmosis (e.g., if the walls of the nanopore carry a charge). If the analyte molecules are charged, they can also be driven through the gap by electrophoresis.

Figure 1:
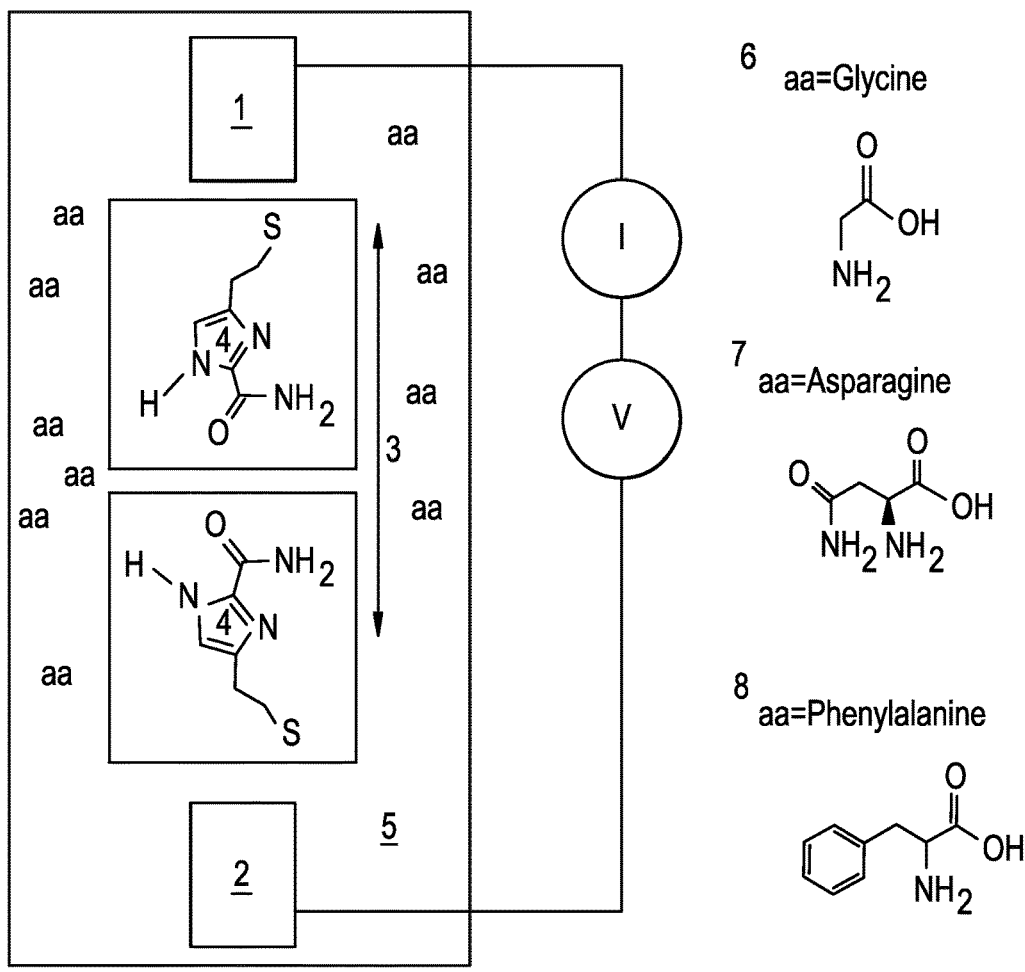
FIG. 1 illustrates a tunnel gap apparatus for detecting analytes that bind transiently to recognition molecules, generating current spikes (I) when a bias (V) is applied across the gap, according to some embodiments of the present disclosure.

FIG. 1 illustrates an arrangement used for collecting tunneling signals according to some embodiments. As illustrated, two opposed electrodes 1, 2 (i.e., a plurality) are separated by a gap 3 of about 2.5 nm, but which could be as small as about 1 nm and as large as about 4 nm (still other embodiments include a gap between about less than 1 nm and larger than 4 nm, for example). Each electrode may be functionalized with a reagent 4 that is chemically-bonded to the electrodes, to form non-covalent bonds with the target molecule. Shown as 4 in FIG. 1 are two 4(5)-(2-mercaptoethyl)-1H imideazole-2-carboxamide molecules where the SH group has lost the H in order to from a bond with the metal electrode. Such molecules may be synthesized as adaptor molecules for reading, for example, DNA bases.[3] Suitable metals for electrodes include platinum, palladium, gold and silver, all of which have been demonstrated theoretically to give excellent coupling with the electronic states of molecules bonded to them in a tunnel junction.[4] In some embodiments, the entire system is immersed in an aqueous electrolyte 5.

For the data presented here, for some embodiments, the buffer is a 1 mM phosphate buffer, having a pH=7.0. Provided that only (sub-micron)$^2$ areas of one of the electrodes are exposed to electrolyte, electrochemical leakage currents in some embodiments are considerably smaller than tunnel current between the electrodes. The gap 3 may be defined by the current I and the voltage V (electrical bias being the voltage, being supplied by a power supply device, and structure I can be a monitoring device for monitoring current). For a voltage of 0.5V applied between the electrodes, a current of 6 pA is indicative of a gap of about 2.5 nm[5] (for example). A bias of 0.5V and a set-point current of 4 pA were used to collect the data shown in FIGS. 2-5. In these conditions, the tunneling signal in aqueous buffered electrolyte solution (i.e., absence of any amino acids) is free of features, having a noise amplitude of about 3 pA. If the gap is made a smaller (e.g., by increasing the current to 6 pA for example) noise spikes of up to about 20 pA appear in the presence of aqueous buffer alone, but these are rare (e.g., a few counts per hour).

Figure 2:
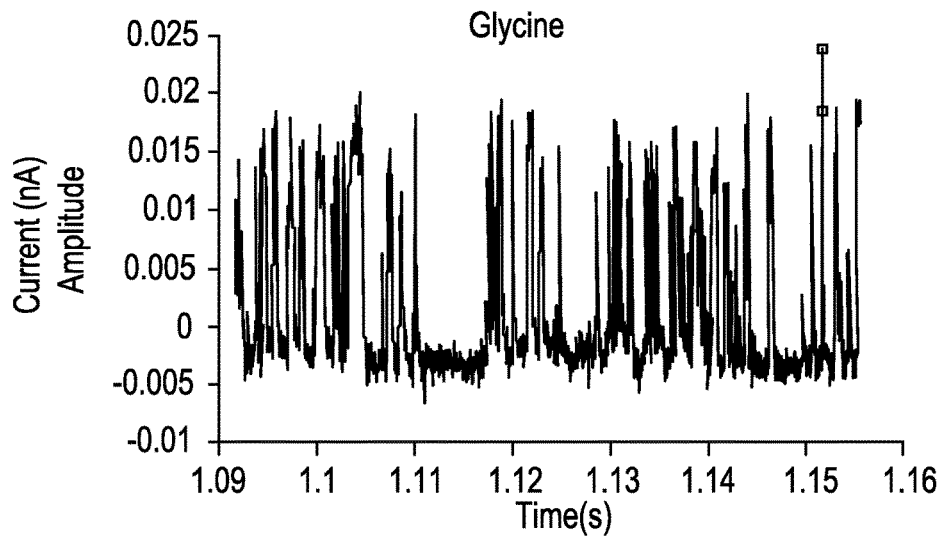
FIG. 2 illustrates exemplary signals from glycine detected using gold electrodes produced by some embodiments of the present disclosure.
Figure 3:
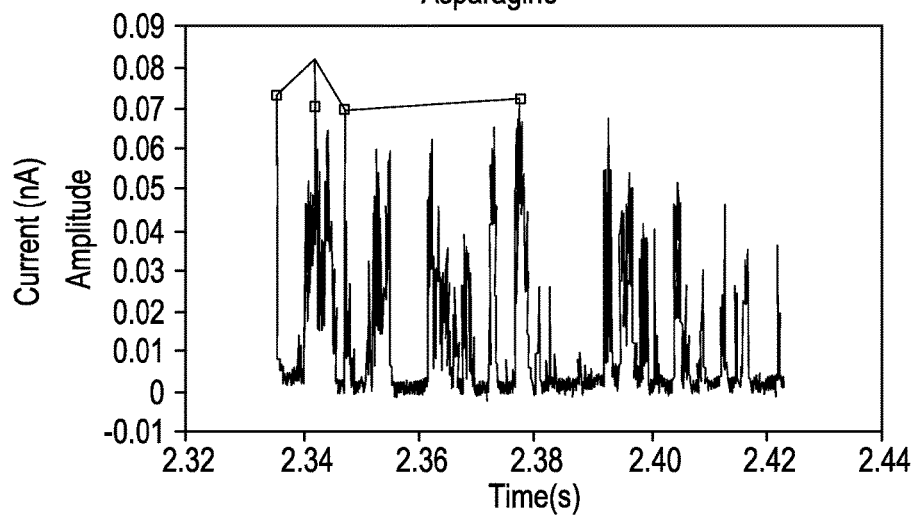
FIG. 3 illustrates exemplary signals from L-asparagine detected using gold electrodes produced by some embodiments of the present disclosure.
Figure 4:
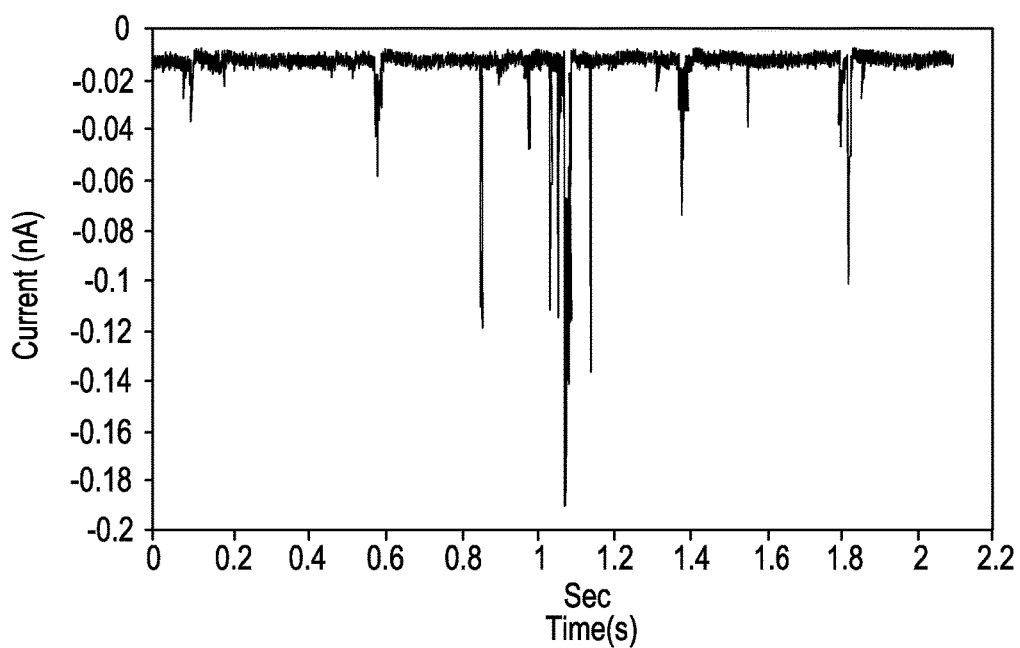
FIG. 4 illustrates exemplary signals from phenylalanine detected using gold electrodes produced by some embodiments of the present disclosure.

In some embodiments, when amino acids are added to the solution ("aa" in FIG. 1), relatively large signals immediately appear, in this case because the analyte molecules drift into the tunnel gap by diffusion. Referring to FIG. 1, data for glycine, 6, asparagine, 7 and phenylalanine, 8 will be described. These amino acids were added at a concentration of 100 micromolar, but smaller concentrations (down to 1 nM for example, in some embodiments) can be used. Each amino acid gives a different characteristic tunneling signal. FIG. 2 illustrates a signal from glycine, produced according to some embodiments of the present disclosure. In this example, the spikes have an average peak height of about 30 pA and a frequency of about 600/hr at this concentration. FIG. 3 illustrates signals from asparagine. Here, the amplitude is higher (about 40 pA on average) as is the frequency (~1000 counts per hour), and the duration of the spikes is also longer. FIG. 4 illustrates data for phenylalanine, where the peaks are large (~100 pA) but infrequent (~100 counts/hr).

Figure 5:
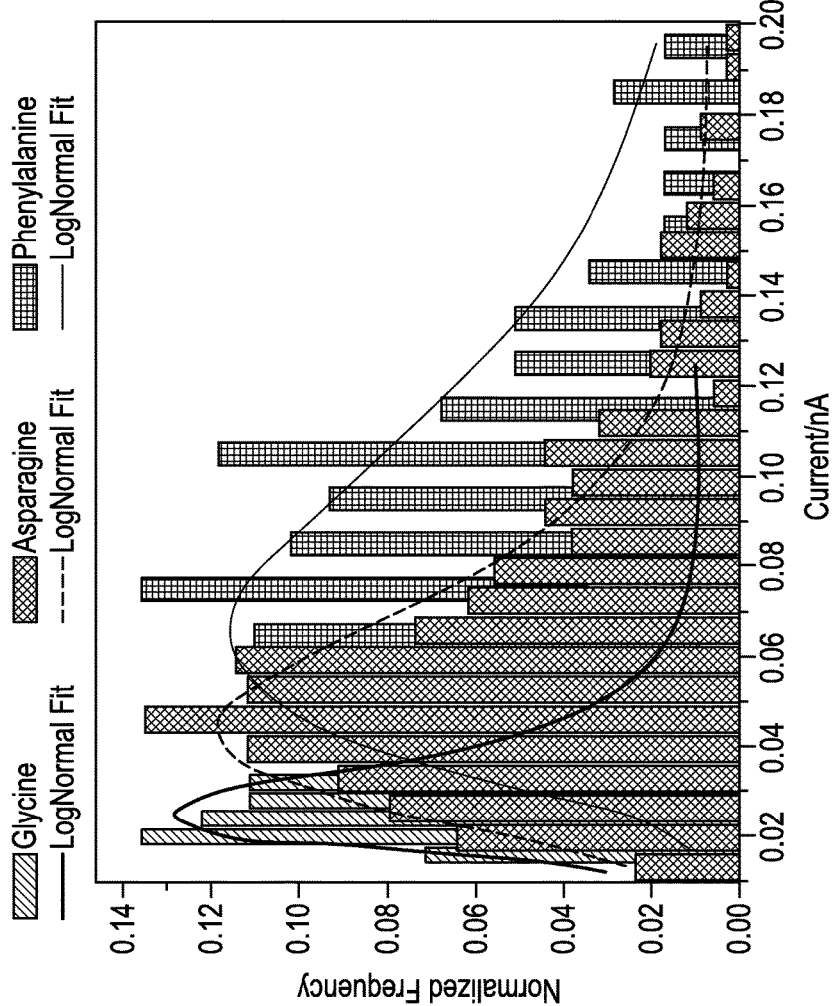
FIG. 5 illustrates distributions of pulse heights from glycine (red) asparagine (blue) and phenylalanine (green) fitted with log-normal functions produced by some embodiments of the present disclosure.

FIG. 5 shows distributions of spike intensities for all three amino acids plotted together and fitted with log-normal distribution functions according to some embodiments. The peak values of the fitted currents are listed in FIG. 6 together with the count rate. In calculating these distributions, all peaks with a width less than or equal to the current amplifier's response time (0.15 ms) were discarded. These data establish that distinct electronic signals are generated by different amino acids in a RT junction.

While there is considerable overlap between the peak height distributions from these three exemplary amino acids, other parameters can be used to make assignments. Examples of such parameters may include:
  Width of the spikes;
  Ratio of "on" to "off" time in a signal burst;
  Duration of a burst of signal;
  Degree of clustering of the peaks;
  Flatness of the top of the spike;
  Frequency of the spikes; and
  Rise and fall times of the spikes
In some embodiments, a combination of these parameters may be used.

In some embodiments, the shape of the spikes may be characterized by the size of frequency components in a wavelet analysis, and any number of components can be included in a principle component analysis, for example, conveniently carried out with Support Vector Machine (SVM) code. Accordingly, with adequate training of a recognition code, an assignment of signals from all 20 of the amino acid residues may be obtained.

Figure 7:
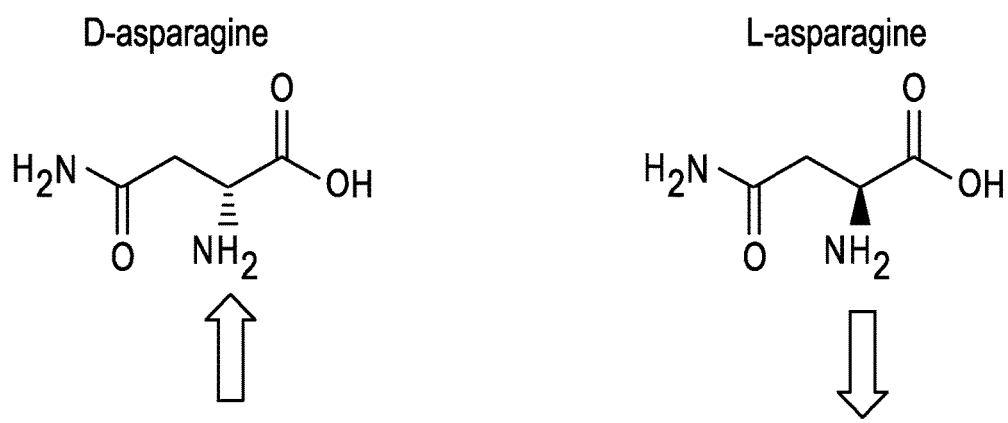
FIG. 7 illustrates optical isomers of asparagine.
Figure 8:
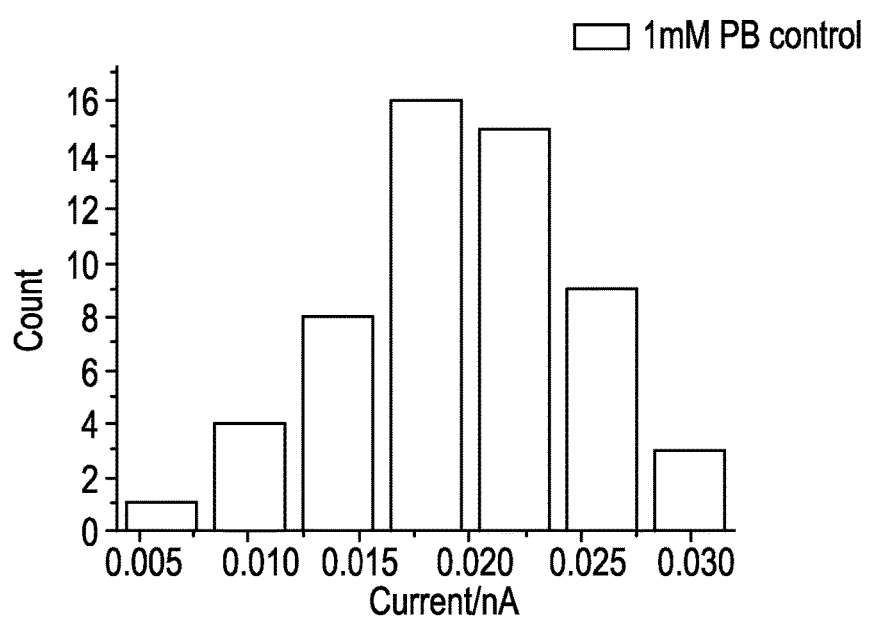
FIG. 8 illustrates distribution of peak heights from aqueous buffer alone using gold electrodes at a bias of 0.8V and a tunnel current of 6 pA, corresponding to a gap conductance of 7.5 pS, produced by some embodiments of the present disclosure.[FN1]

In some embodiments, the system may be sensitive to chirality (i.e., optical isomerism) of individual molecules. Specifically, in some embodiments, the amino acid is trapped by bonding to the recognition molecules in the gap. Thus, the three dimensional details of its non-covalent bonding to the recognition molecules becomes important. To demonstrate this, exemplary data for L-asparagine and D-asparagine is illustrated in FIGS. 9 to 13. The stereo chemistry of the two isomers is displayed in FIG. 7. In D-asparagine, the amine ($NH_2$) group points into the plane of the paper, while in L-asparagine, the amine ($NH_2$) group points out of the plane of the paper. In RT measurements, according to some embodiments, the difference is that D-asparagine produces virtually no signals in the tunneling conditions used to detect L-asparagine (0.5V bias, 4 pA tunnel current, corresponding to a gap conductance of 8 pS). Increasing the tunnel current to 6 pA with the same bias (gap conductance=12 pS) also produced no reads from D-aspargine. However, increasing the bias to 0.8V while leaving the current at 6 pA produced copious reads from both D and L asparagine. In some embodiments, the gap conductance in these conditions is the smallest (7.5 pA), so the ability of the gap to trap a specific type of molecule is not only a function of its size (which is proportional to the logarithm of conductance), but also a function of the electric field in the gap (for example). In these conditions, in some embodiments, the clean background in the absence of analyte may be lost (small current peaks being observed in the absence of an analyte). The distribution of the heights of these background peaks is illustrated in FIG. 8, where the count rate is about 1 peak per minute (e.g., low count rate). A typical signal train produced from some embodiments, from D-asparagine (100 μM D-asparagine in 1 mM phosphate buffer, pH 7.0) is illustrated in FIG. 9, where the count rate is much higher (tens to hundreds of counts per second). The corresponding distribution of peak heights is illustrated in FIG. 10, where the peak value of this distribution is 33.5 pA.

In some embodiments, L-asparagine produces larger signals in these conditions. FIG. 11 illustrates a typical signal train when 100 μM D-asparagine in 1 mM phosphate buffer (pH 7.0) is added to the solution in which the tunnel junction is immersed. The signals may now be less frequent than those from D-asparagine in these tunneling conditions, but the peak heights are larger (for example). The distribution of peak heights is illustrated in FIG. 12, where the peak of a log-normal fit is 58 pA.

The ability of the methods and systems according to some embodiments of the present disclosure to distinguish between two enantiomers at the single molecule level is illustrated in FIG. 13. This figure shows the distribution of pulse heights from an equimolar mix of D- and L-asparagine. The distribution shows two well separated peak currents of 34 pA (D-asparagine) and 60 pA (L-asparagine). On the basis of peak height alone, each peak may be assigned (according to some embodiments). Thus, one can identify one amino acid from another on the basis of its RT signal, and identify enantiomers—and to do so at the single molecule level.

A readout apparatus, according to some embodiments, which enables a scheme for sequencing and/or identifying one or more proteins and/or one or more peptides is illustrated in FIG. 14 (in some embodiments, also including sequencing and/or identifying one or more amino acid, and/or modified amino acid). As shown, a silicon or silicon nitride membrane 130 spans a channel 117 containing an electrolyte solution 108, 109. The membrane, typically about 10 to about 100 nm thickness, divides the channel into two chambers, a cis chamber 108 and a trans chamber 109, in fluid communication with each other only by means of a nanopore 102 that may be drilled through the membrane (and all the other layers 103, 104, 101, 120) by means of, for example, an electron beam. Ideally, the nanopore may be between about 1 and about 5 nm in diameter at the point where it passes through the electrodes. The pore passes through planar electrodes 103, 104 separated by the dielectric layer 101 (for example). The dielectric layer may be between about 1 nm and about 4 nm thickness between the electrodes and may be made by depositing silicon nitride, silicon dioxide or hafnium oxide. The electrodes may be made by depositing between about 1 nm to about 5 nm of silver, gold, palladium or platinum onto the top of the first membrane 130 (for example). The dielectric layer 101 may then be deposited, followed by deposition of a second metallic layer, 104. This "top" electrode may then be covered by a second layer of dielectric 120. Fabrication of the assembly according to some embodiments is completed by drilling the nanopore. One or more of the electrodes (in two-electrode embodiments, e.g., both; in plurality of electrode embodiments, two or more) may then be functionalized by immersing the assembly in a solution of the recognition molecules 107. The molecules is linked to a thiol group via a one or two carbon atom chain, and electrodes may be functionalized using a 0.1 mM to 10 mM solution in ethanol to which the nanopore is exposed overnight (for example).

Each chamber of the apparatus may be filled with an electrolyte such as KCl or $NaClO_3$ (for example), in concentrations that range from about 1 mM to about 1M, and to which may be added Mg ions and/or ATP as required to activate enzymes 113 attached to one or more beads 112 which are fixed in turn to the walls of the channel 117 in close proximity to the nanopore 102. Alternatively, the enzyme is directly attached to the channel in close proximity to the nanopore. The enzymes may then be any one of the well-known proteases which include carboxypeptidase, aminopeptidase, trypsin, chymotrypsin, pepsin, papain or elastase (for example). Since each of these proteases is somewhat selective in their hydrolysis of peptide bonds, the beads may ideally contain a mixture of these enzymes. In some embodiments, the bead may be functionalized with proteosomes, assemblies that sequentially degrade proteins into their component amino acids. The isolated protein or peptide 114 to be identified/sequenced may also bound to the bead. In some embodiments, digestion of the protein may be initiated by binding the protein to the bead in the absence of Mg or other chemicals needed to initiate digestion, the bead placed in the channel, and then digestion is initiated by the addition of Mg or other chemicals (needed to initiate digestion). The resulting small fragments, small peptides, or optimally amino acids 115, may be released into the solution. A bias 118 may be applied between the cis and trans chambers by means of the reference electrodes 111, 110, for example. In the figure, this is shown with the negative electrode in the trans chamber 109. Accordingly, this draws positively charged amino acids and small peptides through the nanopore where they bind transiently to the recognition molecules 107 generating current spikes recorded by a transconductance amplifier 106. A bias 105 of between about 0.1V and about 1V is preferably applied between the electrodes 103, 104. The walls of an oxide layer (such as the surfaces of silicon, silicon nitride or silicon dioxide or hafnium oxide) in aqueous electrolyte are negatively charged 116 owing to the accumulation of OH groups on the surface. This negative charge causes an electro-osmotic flow of water towards the negative electrode 115. Thus, neutral amino acids that diffuse into the vicinity of the nanopore may be swept through it by the electro-osmotic flow of the water.

All the neutral and positively charged amino acid residues can be read by the same nanopore apparatus, according to some embodiments. Accordingly, the amino acid mixture will generate a characteristic set of tunneling signals that will allow the protein or peptide to be identified. To the extent that the digestion of the target proteins is sequential and synchronized, the train of signals could also be used to deduce protein sequence, while the sequence of small peptides may be read directly from the time series of signals generated as each amino acid in the chain passes through the tunnel gap.

Fabrication of the apparatus according to some embodiments is illustrated in more detail in FIG. 15. Accordingly, a silicon substrate 201 is covered with a thin layer of dielectric 202, such as low-stress silicon nitride. This layer may be between about 1 nm and 100 nm in thickness. A window 208 may be etched through the silicon support by an anisotropic etch. A metal electrode layer 203 may be deposited onto the dielectric layer 202. This layer may be any one of silver, gold, palladium or platinum and be between about 1 nm and about 10 nm thick. A layer of Ti or Cr of about 1 nm may be used as an adhesion layer for this metal electrode. A second layer of dielectric 204 may then be deposited onto the metal electrode 203. This dielectric may be silicon nitride, silicon dioxide or hafnium oxide and be between about 1 nm and about 4 nm in thickness. A second metal electrode 205 may then be deposited on top of the dielectric layer 204. This layer may be of the same or similar composition and thickness to that of layer 203. Finally, a layer of dielectric 206 may be deposited on top of the apparatus and is formed (not shown) to contact, for example, each pair of electrode planes at each apparatus. 203, 205. A nanopore 207 of between about 1 and about 5 nm in diameter may then be drilled through the entire assembly. A perspective view of the apparatus is illustrated on the right of FIG. 15, indicating where bias may be applied and/or where current may be read. Each nanopore apparatus in an array may have a separately addressable pair of electrodes, and the area of opposed electrodes may be minimized in order to reduce leakage through the dielectric. Typical opposed areas of electrodes may be about 0.1 micron by about 0.1 micron square.

FIG. 16 illustrates an arrangement according to some embodiments for capturing and reading the negatively charged amino acids and peptide fragments. A second nanopore apparatus 301 may be placed in close proximity to the first apparatus 305 and separates the cis chamber 108 from a second trans chamber 302 isolated from the first trans chamber 109. A third reference electrode 303 may be placed in the second trans chamber 303 but may be biased positively 304 with respect to the cis chamber. Thus, this second nanopore acts to capture the negatively charged residues 306.

FIG. 17 is an illustration of peptide sequencing by directly tunneling reading of amino acid residues, according to some embodiments of the present disclosure.

FIG. 18 is an illustration of peptide sequencing by enzymatically cleaving amino acids from a terminal of protein, according to some embodiments of the present disclosure.

FIGS. 19A-C illustrate characteristic signal traces for 18 of the 20 amino acids together with two examples of control data (upper left panels in 19A and 19C) obtained with buffered electrolyte alone. These data were obtained using palladium electrodes. In this example, the baseline tunnel current was set to 4 pA with the probe biased at +0.5V with respect to the substrate. 100 micromolar aqueous solutions of the amino acids containing 1 mM phosphate buffer (pH=7) were also used. FIG. 19A illustrates recordings for the charged amino acids arginine (Arg), histidine (His), Lysine (Lys), Aspartic acid (Asp) and glutamic acid (Glu). FIG. 19B illustrates recordings for the hydrophobic amino acids, alanine (Ala), Valine (Val), isoleucine (IIL), leucine (Leu), methionine (Mfet) and phenylalanine (Phe). FIG. 19C illustrates recordings for serine (Ser), threonine (Thr), asparagine (Asn), glutamine (Gln), cysteine (Cys), glycine (gly) and proline (pro). The two examples of control data (top left panel in FIGS. 19A and 19C) are free of features with the exception of few sharp spikes seen in a percent or so of the runs (an example is pointed to by an arrow on the panel in FIG. 19C).

In this example, the two most aromatic amino acids, tyrosine and tryptophan, appear not to give signals in these conditions. Signals can be obtained by increasing the tunneling set point to 6 pA and 10 pA respectively, but the signals contain some spurious background from water. This can be removed using a SVM analysis.[7] Thus, in some embodiments, there may be an advantage in having an adjustable tunnel gap (as described in an additional embodiment detailed below).

An SVM[7, 8] trained on 18 amino acid data sets simultaneously, and 3000 peaks were sampled for each of 17 amino acids. The exception was isoleucine, where only 800 peaks were measured. 400 of the 3000 were used for training, and then the remaining 2,600 peaks were called using the resulting support vectors. The accuracy with which the peaks were called is listed in Table 1 below. Tyrosine and tryptophan were excluded from the analysis shown here, but also give distinctive signals.

Thus, individual amino acids may be read with high fidelity based on, in some circumstances, a single signal spike. A final accuracy of a call may depend on how many amino acids cluster near a correct one in parameter space. Should the missed calls be spread among many other amino acids, then the probability of a majority call being incorrect would be even smaller than suggested by the numbers in Table 1.

TABLE 1

Accuracy with which each signal spike is called.

| Amino Acid | Accuracy |
|---|---|
| PHE | 93% |
| ASP | 95% |
| SER | 87% |
| ARG | 84% |
| THR | 93% |
| GLU | 87% |
| HIS | 84% |
| LEU | 83% |
| ASN | 88% |
| GLY | 99% |
| CYS | 78% |
| IIL | 52% |
| MET | 81% |
| PRO | 92% |
| GLN | 82% |
| ALA | 92% |
| LYS | 83% |
| VAL | 89% |

These data were taken with just one run each, and the SVM was trained on a single amino acid at a time. Run to run variations in the tunnel gap were not accounted for, and the problem of identifying multiple analytes from a mixed pool of signals was not addressed. These problems are addressed for a limited pool of amino acids below. Note that the ability to separate leucine and isoleucine is another example of how RT may be used to separate isobaric isomers which are not distinguished by mass spectroscopy in addition to the earlier case of L- and D-Apargine.

In some embodiments, an amino acid/protein sequence reader which eliminates the requirement for a nanopore is provided. The principle of this embodiment is illustrated in FIG. 20A. Accordingly, a protein to be sequenced is immobilized in a reaction chamber 501, where it is degraded step by step from the N-terminus using a heat/acid/base cycle with the Edman reagent.[6] As each aliquot of an amino acid from the chains is released, it is passed to the measurement chamber 503 by means of a microfluidic connection 502. If the measurement and reaction chambers are of similar volume (V1=V2) then all of the sample will be passed into the measurement chamber. An example of a chip for carrying out Edman degradation is given by Chen et al.[9] with aspects of the chip described further in Chen, Shen et al.[10] The chip described uses Edman chemistry to remove one amino acid at a time from the N-terminal chain of a peptide, ejecting an aliquot of each amino acid in a volume as small as 3.5 nanoliters starting from femtomoles of peptide. The removal of N-terminal amino acids remains synchronized across a population for about 30 to about 50 amino acids. Thus, the chip ejects each amino acid in turn starting from the N-terminus into a microfluidic channel. In such embodiments of the peptide sequencer described here, the tunneling electrodes may be placed in a microfluidic channel of such a dimension that the final concentration of amino acid at each read step is in the range of about 10 to about 100 micromolar, though lower concentrations may work, but may also give lower count rates.

In some embodiments, smaller volumes can be utilized, with reaction chambers down to the femtoliter range (for example), given the relatively small tunneling volume between electrodes. In the case of a 3.5 nanoliter reaction volume, for example, a final concentration of $10^{-4}$ moles/liter (which yields hundreds of counts per second in our detector) would require just 350 fM of starting protein. If the volume was reduced to 10 picoliters (a cell of 20 microns on each side), then less than a fM would be needed. In some embodiments, the reading volume and the reaction volume are substantially the same (and in some embodiments, the same) or similar. With appropriate treatment of the microfluidic channels, the only dilution may be caused by diffusion of the aliquot of molecules along the channels. In the case of a 3.5 nanoliter volume, a characteristic channel length is 150 microns. Given that the diffusion constant of a typical amino acid is $8 \times 10^{-6}$ cm$^2$/s, the aliquot requires nearly 30 s to diffuse over this distance. In the case of a 10 picoliter volume, this time is reduced to 0.5 s. Thus, in some embodiments, there is an ample amount of time to move the sample and record recognition signal peaks.

As shown in FIG. 20B, an example of a measurement cell according to some embodiments, with nanoliter volume, is shown and described herein. Accordingly, the aliquot from the reaction chamber is injected via a microfluidic coupling channel 601 into a channel 602 that has a width in the region of 100 microns and a similar height, set by the etching depth 607 into the glass substrate 608. The lower surface 606 is coated with a film of suitable metal such as Pd (for example), which is contacted via an electrical connection (not shown). A metal probe 603, made of a similar metal (usually Pd) having a sharp exposed apex 604 and otherwise covered with insulation (as described by Tuchband et al.[11]) is positioned through a hole 610 in an upper plate 609 that is bonded over the lower assembly to seal the channel 602. The probe apex 604 is placed within tunneling distance of the substrate 606 by means of a scanning tunneling microscope controller as is well known in the art. The apex of the probe 604 is placed a short distance 605 away from the end of the channel 602. If this distance is about 100 microns or less, then a nanoliter of sample passed down the channel 602 floods the tunnel junction between the probe apex 604 and the substrate 606. Providing that the hydrostatic pushing pressure is removed once the aliquot is delivered, it will remain in the vicinity of the junction for at least 30 seconds (as described earlier). Please note, the dimensions described above are merely exemplary, as the scale is readily reducible from about 100 micron distances down to about 20 micron distances or less.

In operation (for example), an aliquot to be measured is passed to the tunneling junction, measured by means of its characteristic tunneling signal, and then flushed out by passing clean buffer into the measurement cell via the channel 601/602. The cycle is then repeated as needed.

Another advantage of using a microfluidic channel with a scanning-tunneling micropscopy (STM) apparatus, according to some embodiments, is that an adjustable tunnel gap can be included for added versatility and ease of manufacture. Such embodiments also may allow identification of species that require a different tunneling gap. For example, in the case of tyrosine and tryptophan, a "null" read in the standard tunneling conditions (0.5V, 4 pA) can be followed rapidly by a sample taken at a smaller gap (6 or 10 pA current) to see if the aliquot of sample that produced no signal was tyrosine or tryptophan. In that way, all 20 amino acids can be identified.

A view of an exemplary nanoliter scale reaction system, according to some embodiments, is shown in FIG. 20C. Two microfluidic channels 702 are etched in the form of a cross in a substrate 700 sealed with a top plate 720. One of the channels 703 contains the nanoliter reaction chamber. Reagents are pushed into this chamber by the pump/dispenser 712. Reaction products are released by opening the valves 708 and 710, where they pass into the output channel 705 to the coupler to the measurement cell 601. For rinse cycles of the reaction cell, valves 708 and 709 are opened, and buffer dispensed by the pump 712. For rinse cycles of the measurement cell, valves 711 and 710 are opened and clean buffer flowed from the dispenser 713 out via the coupler 601.

FIG. 20D illustrates a view down into the reaction chamber (703 in FIG. 20C) according to some embodiments. A weir 810 is formed in the reaction channel 800 by masking part of the channel during etching leaving a space of a few microns at the top of the channel to pass fluid and small molecules but trapping reaction column beads. A nanoliter or so of column material (such as C12[9]) is flowed into the channel where it piles up against the weir to form the reaction cell 802. A heater (not shown) is placed underneath this reaction cell so that the standard cycle of base, acid and heat can be applied to complete the Edman reaction.

The overall assembly, according to some embodiments, is shown in FIG. 20E. The measurement chamber 900 and reaction chamber 901 are coupled via the coupler 601 and may sit on a common base 902 that contains controls for the reaction chip and its heater. The probe 603 is held above the substrate 606 by an actuator 903. This consists of a coarse mechanical approach based on a stepper motor in series with a fine adjustment that uses a piezoelectric material as is well known in the art. This may be coupled to the base 902 via a rigid support 905 and a top housing 904 that holds the actuator and control electronics for the tunnel gap.

Prior to sequencing, both the probe 603 and the substrate 606 may be functionalized with an adaptor molecule as previously described. Buffered electrolyte may then be pushed from a reservoir on the microfluidic chip 901 to fill the reading channel 602 and the probe advanced to the desired tunneling current by means of the actuator 903, and subsequently controlled by the servo circuit. A set point at a bias of 0.5V between the probe and substrate is a current of 4 pA (for example).

The first Edman degradation may then be carried out, and control valves on the microfluidic chip may be set so as to release the first amino acid aliquot released from the peptide into the reading channel up to the point where it is preferably centered on the junction region between the probe apex 604 and the substrate 606. RT signals may then be acquired for a period of between about 0.1 to about 1s and recorded for subsequent analysis. Valves on the microfluidic chip may then be set to flush the sample out of the junction area. Then a next cycle of Edman chemistry may be carried out, releasing the next amino acid to the junction for the next read. This cycle may be repeated out to the limit of reliable cleaving by Edman chemistry, which may be (for example) up to about 50 amino acid residues. In some embodiments, mixtures of amino acids can be analyzed by this technique with each read producing hundreds or thousands of signal peaks, each one of which can be assigned to a particular amino acid, enabling analysis of the data well into a number of amino acids beyond 50 amino acid residues, based on the identity of the last reliably called residue. This is because contaminants from residues that may fail to have cleaved in earlier reactions will have been previously recorded, so their presence in a subsequent reaction can be recognized as an artifact of the chemistry.

Accordingly, in some embodiments, the same ability to make hundreds or even thousands of single molecule calls from even a few femtomoles of sample for each amino acid, which, corresponds to small amounts of post translationally modified amino acids, can be identified.

Analysis of the signals by means of a multiparameter characterization of each pulse is described in the publication by Chang et al.[7] Wavelet and Fourier analysis may be used to characterize the shape of each pulse in the signal train and a SVM[8] to assign the pulse using data obtained from known calibration samples. Using a systematic search of parameter combinations, the SVM may be trained to recognize new data with an accuracy that can exceed 90% based on just one pulse of the data train. Thus, many calls will be made for each aliquot of amino acids that pass into the reader channel.

In some embodiments, a fixed tunnel gap can generate RT signals from an amino acid. FIG. 21A illustrates an exemplary apparatus for sequencing an amino acid according to some embodiments. A tunnel gap crafted by cutting a palladium wire 2101 on a silicon nitride substrate with an electron beam. A drop of analyte 2103 is placed onto the gap and signals collected. FIG. 21B illustrates a transmission electron microscopy image (TEM) of a gap prior to functionalizing with imidazole carboxamide recognition molecules—the smallest part of the gap in this image is 2.07 nm. FIG. 21C illustrates the signals generated with just phosphate buffer (pH7), and FIG. 21D shows the signals generated after adding 100 micromolar glycine, which shows the current spikes when molecules of glycine pass through the tunnel gap.

The data analysis shown in Table 1 was restricted to just one run for each amino acid tested with the true positive rate quoted for the SVM trained on a subset of the data in that run so they do not reflect the important influence of variations in the atomic details of the tunnel junction form experiment to experiment. Here, it is shown that amino acids may be reproducibly identified across different measurements with different tunnel junctions set to the same set point current. In order to determine transferability of data, a study was conducted on a limited number of amino-acids. Since no two tunnel junctions are identical at the atomic level, that is, signals will likely be different form device to device, the following measurements correspond with four different junctions to find characteristics of the signals that are conserved from junction to junction. In addition, an investigation was conducted to determine whether the technique would discriminate between those molecules that are challenging for mass spectral analysis, without the aid of other techniques.

Accordingly, leucine and isoleucine (isobaric isomers), L-asparagine and D-asparagine (as an example of enantiomers), L-arginine (with a charged side chain) and glycine (with no side chain), were chosen for analysis. Data was generated according to the following constraints: (1) control runs (phosphate buffer alone with concentration in the range of 1.0 to 10.0 mM) were free of any features (indicating that the buffer solution was free of contaminants); (2) insulated STM probes had to show no electrochemical leakage down to below the measurement limit (<1 pA)—electrochemical leakage is sensitive to the tip-to-surface distance and cannot be simply backed out of the signal. Thus, leakage often introduces an error into the tunneling current set point, resulting in variability of the tunnel gap from experiment to experiment.

Finally, data from four (4) runs (meeting the above criteria) for each sample was collected. A key collected criterion was to find one or more signal parameters that varied systematically from analyte to analyte, but that remained constant with repeated runs (using different junctions) on the same analyte. Examples of signals from L-leucine and L-isoleucine are shown in FIGS. 22A and 22B. In these figures, the parameters are shifted so that zero (0) on each axis is the mean value for six (6) amino acids measured (in four separate experiments each). The scale is normalized to the standard deviation of the distributions for all six (6) amino acids. In this two-parameter analysis, most of the data is overlapped (white area of the probability density function). A 14 component analysis separates isoleucine from the other 4 amino acids to 90% true positive rate for each spike in the signal train. When a large data set is analyzed, amplitudes are exponentially distributed and cover a wide range, but the distribution shows that there is a significant difference in the tails of the distribution (FIGS. 22C and 22D).

The plots show scatter plots for peak widths and amplitudes (symbols) overlaid on the fitted probability distribution functions used by the SVM. The circled region shows that isoleucine can generate significantly larger peaks than leucine. This is a notable result, since the structural difference between these two amino acids is small and subtle (see insets in FIGS. 22A and 22B). The SVM can use up to 30 parameters that characterize each pulse in a data train, including parameters that characterize the pulse shape as well its relation to neighboring pulses in a signal train.[7]

The parameter sets were first subjected to a covariance analysis and parameters that were highly correlated were rejected (so do not convey new information). Other parameters were rejected whose distributions vary from data set to data set with the same analyte. This reduced the subset of useful parameters to 14. Using these parameters, the SVM was trained on small subsets of the data, and then analyzed all of the remaining data (pooled from all six amino acids). The results of which are illustrated below in Table 2 (parameter combinations not optimized).

TABLE 2

SVM analysis of 318,000 signal spikes from pooled data from 6 amino acids, using 4 tunnel junctions each (Wrong Calls are the fraction of other amino-acid signals called as the amino acids listed - numbers do not sum to 1 as wrong calls are randomly distributed among all amino acids.). Signal parameters analyzed were selected to be robust against variations from junction to junction.

| Amino Acid | True Positives | Wrong Calls |
|---|---|---|
| Arginine | 0.55 | 0.07 |
| D-asparagine | 0.78 | 0.09 |
| L-asparagine | 0.84 | 0.08 |
| Isoleucine | 0.51 | 0.05 |
| Leucine | 0.82 | 0.01 |
| Glycine | 0.84 | 0.08 |

Random calling of a peak would result in a 17% probability of a correct call. Even at this early stage, a single peak can call an amino acid with better than 0% true positive rate (with 90% discrimination between pairs such as leucine and isoleucine). Each trapped analyte generates many peaks.

Post translational modifications play an extremely important role and detecting them can require very high resolution mass spectroscopy. Here it is shown that a modified amino acid is readily identified from within a larger pool of analytes. Signals were obtained from sarcosine (methylglycine), again running at least four repeated experiments with different tunnel junctions (FIG. 22E, panel e). The entire pool was then subjected to the SVM analysis as described above. The results for this pool (now of seven analytes) are shown in FIG. 22F. Individual peaks are assigned to sarcosine with a true positive rate that exceeds 80%.

Examples: Accuracy, Sample Concentrations and Amounts of Sample

Table 3 below illustrates a comparison of analytical methods for detection of amino acids and peptides.

correct calls will occur one time in four (4) reads (1/(0.5)2). Two (2) incorrect calls of the same kind occur only one (1) in twenty (20) times (e.g., 1/(0.5×0.1). The remaining outcomes consist of ambiguous reads with two (2) different calls. The accuracy improves rapidly with the number of spikes sampled as shown in FIG. 23a (probability of a wrong call vs. number of current spikes). This may be at the cost of an increased number of reads that do not pass the "majority vote" test, which, in a large train of spikes, may be too stringent. Other strategies for optimizing the required size of the winning block vote to maximize accuracy while minimizing the amount of wasted data, can be used and determined by testing them with Monte Carlo sampling of real data (for example). In some embodiments, bursts with high information content may be clustered, and thus, may be used to further refine data selection for SVM training. This is illustrated with measurements of the experimental true-positive rate for the entire pool of data for the seven amino acids whose spectra were shown in FIG. 22F. FIG. 23b shows the measured true positive rate as a function of the number of sequential signal spikes that make the same call. Using only those signals that are called the same way for 8 spikes in a row increases the true positive rate from 70% to 99%.

Lower Concentrations. The collected data outlined in FIGS. 21 and 22 were taken with concentrations of between about 1 to about 100 μM of target molecule using a large volume liquid cell on a conventional STM. The collected data may be a consequence of the experimental design: in such experiments, the tunnel gap was set up in clean buffer and thereafter, the sample of amino-acid added after control signals were obtained. Accordingly, target molecules have to diffuse large (many microns) distances to get into the tunnel gap. Two strategies are explored: dielectrophoresis and pressure-flow.

With dielectrophoresis, by applying alternating current (AC) fields to the tunnel gap, charged and dipolar molecules can be concentrated into the gap. Accordingly, in some embodiments, a one-dimensional STM (FIG. 20B) is pro-

TABLE 3

| Analytical Method | Sample | Lowest detection Concentration | Sample Volume | Quantity Detected | Linear Range | Reference |
|---|---|---|---|---|---|---|
| LC-IMS-MS | Fibrinopeptide A | 0.7 nmole/L (1.0 ng/mL)* | 5 μL | 3.6 fmole | 0.001 to 10 μg/mL | J. Proteome Res. 2010, 9, 997-1006 |
| ICE-MS | Amino acids | 0.5 μmole/L | NR* | — | 0.5 to 2500 μmol/L | J. Chromatography B 2011, 879, 2695-2703 |
| CE F-labeling | Amino acids | 6 pmole/L | 30 μL | 180 attomole | NR | Anal. Chem. 2010, 82, 2373-2379 |
| LC-QTRAP | Peptides | 0.4 nmole/L (0.4 fmole/μL)* | 25 μL | 10 fmole | 1-500 fmole/μL | Nature Biotechnology, 2009, 27, 633-641 |
| RT (Targeted) | Amino Acids | 1 nmole/L | 5 μL | 5 fmole (unlabeled) | Digital Counting | |

While recognition tunneling has potential advantages in terms of sensitivity, lack of labeling and single molecule counting, the accuracy of the assignment of single molecule signals can be improved. In some embodiments, accuracy is better than the true positive rate shown in Table 3 since each trapped molecule generates multiple spikes (e.g., at least 10 or more). In some embodiments, one way to exploit the repeated data is to use, for example, a majority vote algorithm. For example, if the case of a pool of six (6) amino acids with a 0.5 true positive rate considered, with the remaining calls being distributed amongst the five (5) remaining miscalls with 0.1 probability each, then two (2)

vided which may be stable enough to permit periods of servo-control of the gap, which may be interleaved with periods where the tip potential can be altered in an arbitrary manner. In some embodiments, the solution potential (controlled by a reference electrode) is altered to trap molecules in the tunnel gap, which, in some embodiments, sub nM concentrations may be possible.

With pressure-flow, microfluidic cells are provided configured to inject the sample in μl (for example) quantities adjacent to the tunnel gap, and includes a flow profile configured to maximize injection into the gap itself. In such embodiments, this may reduce the absolute amount of sample needed. An exemplary embodiment is show in FIG. 24, where pressure injection (arrow) into the tunnel gap 2402 in a microfluidic cell 2400 is shown. A probe 2404 penetrates a Polydimethylsiloxane (PDMS), microfluidic cover (not shown).

In some embodiments, the recognition tunneling, amino-acid analysis system may be integrated with a high-performance liquid chromatography (HPLC) system. As illustrated in FIG. 10, alone HPLC suffers from incomplete separation of the analytes, an issue addressed by the addition of mass spectrometry (MS). The combined HPLC-MS has achieved limit of detection (LOD) of 2 pico-mole for amino acids without derivatization of amino acids. While it has been demonstrated using isotope dilution and high-resolution mass spectrometry without derivatization and chromatography of amino acids, such a technique required hundreds of pico-mole of peptide.[12] Accordingly, some embodiments of the present disclosure combine recognition tunneling with HPLC to achieve an improved system, which, in some embodiments, yields advantages in the identification of steric isomers and isobaric molecules, a concentration limit in the nM range, a sample volume of microliters, and an LOD below pico-moles. Thus, recognition tunneling (RT) coupled to an HPLC column is an alternative to HPLC-MS. To that end, since some such embodiments of an RT-HPLC can be effected as a simple sequential analysis system, the one-dimensional STM of FIG. 20B may be used.

In some embodiments, the RP-HPLC includes a flow rate of about 0.1 mL/min with the microfluidic flow cell shown in FIG. 24. Accordingly, in some embodiments, amino acids injected into the column generate a tunneling chromatogram of the sample. Liquid chromatographic methods that may be used include, for example, ion exchange (IC), reverse phase (RP), and hydrophilic interaction liquid chromatography (HILIC). In some embodiments of the RP-HPLC, the elution buffer is optimized to ensure that the tunnel junction is cleared rapidly after each read.

Example—Reads of Peptides

Thus far, data for amino acids and modified amino acids has been shown. Since the ends amino and carboxy termini might be expected to interact strongly with the recognition molecules, it is not obvious that peptide chains will generate signals. FIG. 23C shows a typical signal train from a glycine trimer, demonstrating that peptides will produce recognition tunneling signals.

Example—Sequencing

FIG. 26 illustrates a micro-reactor coupled to an RT system which may be used to carry out peptide sequencing. It has been reported that 19 amino acids of a peptide were sequenced by monitoring its carboxypeptidase digest products on line using electrospray ionization (ESI) mass spectrometry.[13] In some embodiments, micro-beads functionalized with exopeptidase are constrained in the micro-reactor to hydrolyze peptides to be sequenced and release individual amino acids. The reaction solution is flushed to the chamber of the RT system for analysis. A series of RT spectra are recorded as a function of incubation time. As illustrated in FIG. 27, which shows sequencing a peptide by RT in combination with enzymatic hydrolysis, each spectrum contains information on amino acid compositions released at a given time, from which the sequence of a peptide is deduced. For example, in one embodiment, peptides were devised to include either random or repeated amino acid sequences and carboxypeptidase Y (CPY), the most commonly used enzyme to determine amino acid sequences of peptides will be used to sequence the peptide.[14] Other embodiments may use carboxypeptidase P.[15]

Various implementations of the embodiments disclosed above (e.g., protein, amino acid and/or peptide sequencing), in particular at least some of the processes discussed, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other.

For example, as shown in FIG. 28, such a system 2800 may include at least one sequencing device 2802 (or molecule detection device, and other disclosed embodiments thereof), which is in communication (wired or wireless) with controller/processor 2804. Processor 2204 communicates with database 2806, which may store signatures for various amino acids, peptides and proteins, as well as collected data from sequencing runs. The processor may include computer instructions operating thereon for accomplishing any and all of the methods and processes disclosed in the present disclosure, including comparing collected current spike data to signatures stored in the database. Input/output means 2808 may also be included, and can be any such input/output means known in the art (e.g., display, printer, keyboard, microphone, speaker, transceiver, and the like). Moreover, in some embodiments, the processor and at least the database can be contained in a personal computer or client computer which may operate and/or collect data from the sequencer. The processor also may communicate with other computers via a network (e.g., intranet, internet).

Similarly, FIG. 29 illustrates a sequencing system 2900 according to some embodiment which may be established as a server-client based system, in which the client computers are in communication with sequencers. The client computers may be controlled by a server 2912, each of which may include the database for storing current signatures of amino acid, peptide and proteins, and also be used to collect data (e.g., either or both may include the database). The client computers communicate with the server 2912 via a network 2910 (e.g., intranet, internet). Each sequencer device 2902*a*, 2902*b*, may each be connected to a dedicated client 2904*a*, 2904*b*.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to protein/peptide/amino-acid sequencing. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

REFERENCES

1. Huang, S.; He, J.; Chang, S.; Zhang, P.; Liang, F.; Li, S.; Tuchband, M.; Fuhrman, A.; Ros, R.; Lindsay, S. M., Identifying single bases in a DNA oligomer with electron tunneling. *Nature Nanotechnology* 2010, 5, 868-73.
2. Lindsay, S.; He, J.; Sankey, O.; Hapala, P.; Jelinek, P.; Zhang, P.; Chang, S.; Huang, S., Recognition Tunneling. *Nanotechnology* 2010, 21, 262001-262013.
3. Liang, F.; Li, S.; Lindsay, S.; Zhang, P., Chemical and Hydrogen Bonding Properties of Imidazole-2-carboxamide, a reagent for DNA Sequencing by Recognition Tunnelling *Chemistry* 2011, submitted.
4. Lawson, J. W.; Bauschlicher, C. W., Transport in Molecular Junctions with different molecular contacts. *Physical Review B* 2006, 74, 125401.
5. Chang, S.; He, J.; Zhang, P.; Gyarfas, B.; Lindsay, S., Analysis of Interactions in a Molecular Tunnel Junction. *J. Am Chem Soc* 2011, 133, 14267-14269.
6. Hempel, J., An orientation to Edman chemistry. In *Modern Protein Chemistry*, Howard, G. C.; Brown, W. E., Eds. CRC Press: 2002; pp 103-122.
7. Chang, S., S. Huang, H. Liu, P. Zhang, R. Akahori, S. Li, B. Gyarfas, J. Shumway, B. Ashcroft, J. He, and S. Lindsay, *Chemical Recognition and Binding Kinetics in a Functionalized Tunnel Junction*. Nanotechnology, 2012.
8. Chang, C.-C. and C.-J. Lin, *LIBSVM: a library for support vector machines*. ACM Transactions on Intelligent Systems and Technology, 2011: p. 2:27:1-27:27.
9. Chen, W., X. Yin, J. Q. Mu, and Y. Yin, *Subfemtomole level protein sequencing by Edman degradation carried out in a microfluidic chip*. Chem. Commun., 2007: p. 2488-2490.
10. Chen, W., J. Shen, X. Yin, and Y. Yin, *Optimization of microfabricated nanoliter-scale solid-phase extraction device for detection of gel-separated proteins in low abundance by matrix assisted laser desorption/ionization mass spectrometrry*. Rapid Communications in Mass Spectrometry, 2007. 21: p. 35-43.
11. Tuchband, M., J. He, S. Huang, and S. Lindsay, *Insulated gold scanning tunneling microscopy probes for recognition tunneling in an aqueous environment*. Rev, Sci. Instrum., 2012. 83: p. 015102.
12. Louwagie, M.; Kieffer-Jaquinod, S.; Dupierris, V.; Coute, Y.; Bruley, C.; Garin, J.; Dupuis, A.; Jaquinod, M.; Brun, V., *Introducing AAA-MS, a Rapid and Sensitive Method for Amino Acid Analysis Using Isotope Dilution and High-Resolution Mass Spectrometry*. J. Proteome Res. 2012, 11, p. 3929-3936.
13. Rosnack, K. J.; Stroh, J. G., *C-Terminal Sequencing of Peptides Using Electrospray Ionization Mas Spectrometry*. Rapid Commun. Mass Spectrom. 1992, 6, 637-640.
14. Walker, J. M.; Winder, J. S., *C-Terminal Sequence Analysis with Carboxypeptidase Y*. In The Protein Protocols Handbook, Walker, J. M., Ed. Humana Press Inc.: 1996; pp 569-571;
15. Yan-Fei, G.; Hong-Xia, W., *Development of C-terminal Sequencing Analysis of Protein and Peptide*. Chin J Anal Chem 2007, 35, 1820-1826.

What is claimed is:

1. An apparatus for sequencing a molecule comprising:
   at least a first and a second electrode;
   a dielectric layer of between about 1 nm and about 4 nm separating the first and second electrodes;
   a membrane between about 10 to about 100 nm in thickness;
   a channel containing an electrolyte solution, wherein the membrane spans and divides the channel to form a cis chamber and a trans chamber,
   wherein the cis chamber and the trans chamber are in fluid communication with one another via a nanopore, and a bead in the cis chamber and arranged within 150 μm of the nanopore, the bead including a molecule for sequencing and/or identifying bound thereto,
wherein:
the nanopore is formed on the same substrate as the pair of electrodes,
the nanopore is between about 1 nm and about 5 nm in diameter at the point where it passes through the electrodes, and
the electrodes include between about 1 nm to about 5 nm of silver, gold, palladium and/or platinum, and the electrodes are functionalized.

2. The apparatus according to claim 1, wherein each chamber is filled with an electrolyte comprising at least one of KCl and NaClO3 in a concentration between about 1 mM to about 1M.

3. The apparatus according to claim 1, wherein the bead includes enzymes attached thereto which are fixed in turn to the walls of the channel.

4. The apparatus according to claim 3, wherein the enzymes comprise proteases selected from the group consisting of trypsin, chymotrypsin, pepsin, papain, elastase and combinations thereof.

5. The apparatus according to claim 3, wherein the bead is functionalized with proteosomes to sequentially degrade proteins into their component amino acids.

6. The apparatus according to claim 3, wherein the molecule comprises an isolated protein or peptide.

7. The apparatus according to claim 1, further comprising one or more reference electrodes.

8. The apparatus according to claim 1, wherein the bead is affixed to the wall of the channel.

9. The apparatus according to claim 1, wherein the molecule is not a protease.

* * * * *